(12) United States Patent
Badawi et al.

(10) Patent No.: US 10,090,070 B2
(45) Date of Patent: *Oct. 2, 2018

(54) ELECTRONIC DENTAL CHARTING

(71) Applicant: ORAL4D SYSTEMS LTD., Calgary (CA)

(72) Inventors: Hisham M. A. Badawi, Calgary (CA); Lloyd Summers, Calgary (CA); Alan Chen, Calgary (CA)

(73) Assignee: Hisham Badawi, Calgary, Alberta (CA)

( * ) Notice: Subject to any disclaimer, the term of this patent is extended or adjusted under 35 U.S.C. 154(b) by 377 days.

This patent is subject to a terminal disclaimer.

(21) Appl. No.: 14/928,266

(22) Filed: Oct. 30, 2015

(65) Prior Publication Data

US 2016/0055312 A1 Feb. 25, 2016

Related U.S. Application Data

(63) Continuation-in-part of application No. 14/847,588, filed on Sep. 8, 2015, now Pat. No. 9,792,413, which
(Continued)

(51) Int. Cl.
*G06F 17/50* (2006.01)
*G16H 50/50* (2018.01)
(Continued)

(52) U.S. Cl.
CPC ............ *G16H 50/50* (2018.01); *A61C 7/002* (2013.01); *G06F 19/3437* (2013.01);
(Continued)

(58) Field of Classification Search
USPC ............ 703/2; 705/3; 433/24, 215; 382/131
See application file for complete search history.

(56) References Cited

U.S. PATENT DOCUMENTS 6,402,707 B1 6/2002 Ernst
7,613,527 B2 11/2009 Raby et al.
(Continued)

FOREIGN PATENT DOCUMENTS

EP 1810204 B1 7/2007

OTHER PUBLICATIONS

USPTO, Office Action for U.S. Appl. No. 15/342,229 dated Apr. 19, 2017.
(Continued)

*Primary Examiner* — Thai Phan
(74) *Attorney, Agent, or Firm* — Norton Rose Fulbright Canada LLP

(57) ABSTRACT

Systems, methods, electronic devices and computer-readable media for charting dental information are described. The method includes generating or retrieving a dental data set including separately-modifiable parameters defining dental information relative to a base parametric model, the parameters providing information for generating signals for displaying a three-dimensional (3D) representation of at least a portion of a dentition represented by the dental data set; receiving an input via the 3D representation; and based on the received input, adjusting at least one of the parameters.

20 Claims, 34 Drawing Sheets

Related U.S. Application Data is a continuation-in-part of application No. 14/258,459, filed on Apr. 22, 2014, now Pat. No. 9,158,889.

(60) Provisional application No. 61/816,332, filed on Apr. 26, 2013.

(51) Int. Cl.
  *G06F 19/00* (2018.01)
  *A61C 7/00* (2006.01)
  *A61C 13/00* (2006.01)
  *G06Q 10/10* (2012.01)
  *G06Q 50/22* (2018.01)
  *G06Q 50/24* (2012.01)

(52) U.S. Cl.
  CPC .......... *A61C 13/0004* (2013.01); *G06Q 10/10* (2013.01); *G06Q 50/22* (2013.01); *G06Q 50/24* (2013.01)

(56) References Cited

U.S. PATENT DOCUMENTS

| | | | |
|---|---|---|---|
| 7,766,653 B2 | 8/2010 | Manemann et al. | |
| 8,060,236 B2 | 11/2011 | Hilliard | |
| 8,194,067 B2 | 6/2012 | Raby et al. | |
| 8,416,984 B2 | 4/2013 | Liang et al. | |
| 2002/0194029 A1 | 12/2002 | Guan et al. | |
| 2003/0139834 A1 | 7/2003 | Nikolskiy et al. | |
| 2004/0236608 A1 | 11/2004 | Ruggio et al. | |
| 2005/0010450 A1 | 1/2005 | Hultgren et al. | |
| 2005/0089822 A1 | 4/2005 | Geng | |
| 2006/0069591 A1 | 3/2006 | Razzano | |
| 2006/0285636 A1 | 12/2006 | Razzano | |
| 2007/0226005 A1 | 9/2007 | Smith et al. | |
| 2009/0198514 A1* | 8/2009 | Rhodes | G06F 19/322 705/3 |
| 2009/0291417 A1* | 11/2009 | Rubbert | A61C 7/00 433/215 |
| 2010/0121658 A1* | 5/2010 | Kaminski | A61C 19/00 705/3 |
| 2010/0179789 A1 | 7/2010 | Sachdeva et al. | |
| 2011/0104630 A1* | 5/2011 | Matov | A61C 7/00 433/24 |
| 2011/0184762 A1* | 7/2011 | Chishti | A61C 7/00 705/3 |
| 2011/0191075 A1 | 8/2011 | Hultgren et al. | |
| 2011/0269097 A1 | 11/2011 | Sporbert et al. | |
| 2012/0179492 A1* | 7/2012 | Rhodes | G06F 19/322 705/3 |
| 2012/0189182 A1* | 7/2012 | Liang | A61C 19/00 382/131 |
| 2013/0297275 A1 | 11/2013 | Sanchez | |
| 2013/0317800 A1* | 11/2013 | Wu | A61C 13/0004 703/11 |
| 2014/0023984 A1* | 1/2014 | Weatherly | A61B 1/00016 433/31 |

OTHER PUBLICATIONS

Delrose & Steinberg, "The Clinical Significance of the Digital Patient Record." JADA, 131(suppl 1):57S-60S, 2000.

Periodontal Chart Online, available at http://www.periodontalchart-online.com/uk/index.asp#, access Jun. 9, 2014.

Rykov, "Three Dimensional Interactive Dental Charting." Oulu University of Applied Sciences Bachelor's thesis, 2012.

United States Patent and Trademark Office, Office Action dated Aug. 1, 2014, issued in U.S. Appl. No. 14/258,459.

United States Patent and Trademark Office, Office Action dated Feb. 26, 2015, issued in U.S. Appl. No. 14/258,459.

United States Patent and Trademark Office, Notice of Allowance dated Jun. 15, 2015, issued in U.S. Appl. No. 14/258,459.

European Patent Office, extended European Search Report issued in European Patent Application No. 17187854.9 dated Jan. 5, 2018.

Anonymous: "Dental Explorer 3D Tutorial 06 3D-Bedienleiste deutsch", , Mar. 14, 2012 (Mar. 14, 2012), XP055436437, Retrieved from the Internet: URL:https://www.youtube.com/watch?v=p6mO-IpDGOM [retrieved on Dec. 19, 2017).

QuintessencePublishing: "Dental Explorer 3D Tutorial 06 3D—Bedienleiste deutsch", , Mar. 14, 2012 (Mar. 14, 2012), XP054977967, Retrieved from the Internet: URL:https://www.youtube.com/watch?v=p6m0-IpDGOM [retrieved on Dec. 19, 2017].

* cited by examiner

Tooth movement

Tooth rotation

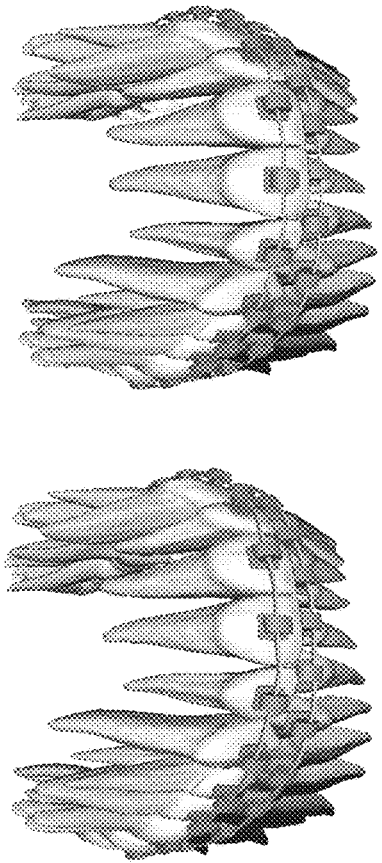

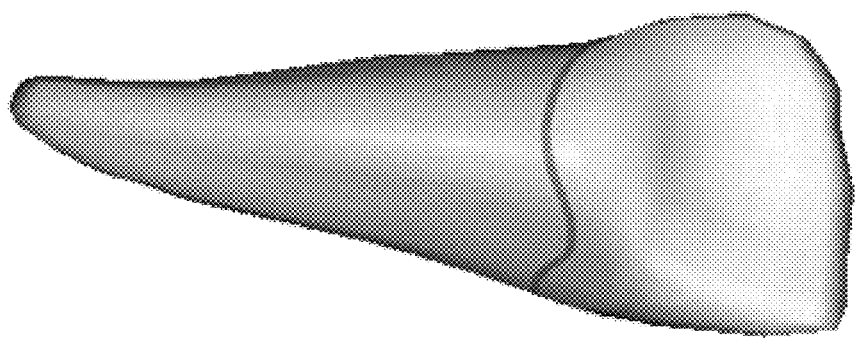
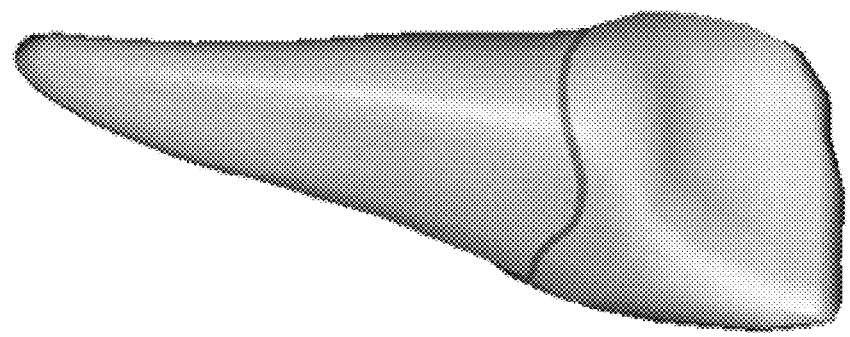
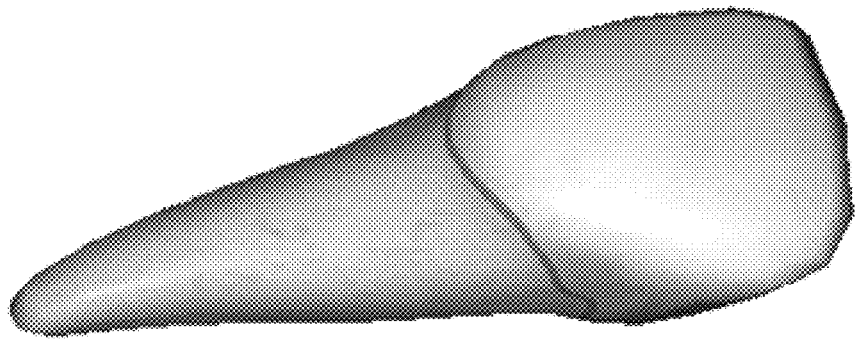
FIG. 43

ELECTRONIC DENTAL CHARTING

CROSS-REFERENCE TO RELATED APPLICATIONS

This application is a continuation-in-part of U.S. patent application Ser. No. 14/847,588, filed Sep. 8, 2015, which claims priority to U.S. patent application Ser. No. 14/258,459, filed Apr. 22, 2014, which claims the benefit of U.S. provisional application 61/816,332 filed Apr. 26, 2013, and entitled ELECTRONIC DENTAL CHARTING; the entireties of all of which are hereby incorporated by reference.

FIELD OF THE INVENTION

The disclosure relates to the field of dental charting, and more particularly to the field of dental charting on an electronic device.

BACKGROUND OF THE INVENTION

Documentation via dental charting has been used for several decades by dental practitioners to help in treatment planning, as well as to represent a record of the condition of the patient's mouth. Historically, dental charts are created on paper. A typical paper chart shows two-dimensional line drawings of permanent dentition teeth. The teeth are illustrated in isolation in linear rows with spaces between each tooth to allow room for a dental practitioner to make hand-written notes to denote different dental conditions or restorations. A dental chart can include a periodontal chart having a series of lines to allow hand-written marks designating pocket depth.

Dental charting software development has followed traditional paper-based charting and commonly provides a display of a traditional paper chart showing linear rows of spaced-apart teeth which can be marked up by a dental practitioner.

SUMMARY OF THE INVENTION

In various aspects, the present disclosure provides systems, methods, electronic devices and computer-readable media for charting dental information. For example, in accordance with one aspect, the present disclosure provides a method for charting dental information. The method includes generating or retrieving a dental data set including separately-modifiable parameters defining dental information relative to a base parametric model, the parameters providing information for generating signals for displaying a three-dimensional (3D) representation of at least a portion of a dentition represented by the dental data set; receiving an input via the 3D representation; and, based on the received input, adjusting at least one of the parameters.

In some aspects, the method includes generating charting text based on at least one charting template associated with a dental activity corresponding to the input received via the 3D representation.

In accordance with another aspect, the present disclosure provides an electronic device for charting dental information. The device includes at least one memory; and at least one processor. The at least one processor is configured to: generate or retrieve a dental data set including separately-modifiable parameters defining dental information relative to a base parametric model, the parameters providing information for generating signals for displaying a three-dimensional (3D) representation of at least a portion of a dentition represented by the dental data set; receive an input via the 3D representation; and, based on the received input, adjust at least one of the parameters.

In accordance with another aspect, the present disclosure provides example methods and devices wherein portions of a dental chart can be navigated and modified through interaction with a visual representation of the dental chart.

In accordance with another aspect, the present disclosure provides example methods wherein a single or multiple dental or medical 3D visual charts can be converted into an independent and standalone format which stores the information contained therein. The format may contain the information in whole, in part, or in condensed form, which may be textual or visual.

BRIEF DESCRIPTION OF THE DRAWINGS

By way of example, reference is now made to the accompanying drawings, in which:

FIGS. 7A-D, 8-12, 13A-D, 14A-B, 15A-D, 16-21, 23-32, 33A-B, 34-38, and 43 to 47 show example visual representations of at least portions of a dental chart.

DETAILED DESCRIPTION

Figure 1:
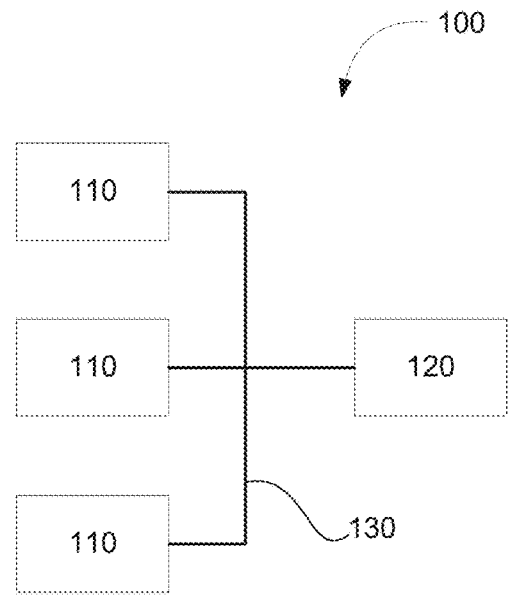
FIG. 1 shows an example system suitable for charting dental information.

FIG. 1 shows an example system 100 for electronic dental charting. In some examples, aspects of the system can be used to help a dental practitioner to create and maintain a patient dental chart on an electronic device. Aspects of the example systems can, in some examples, be a component of a larger management information system to assist in dental practice management.

For the purposes of this disclosure, the term dental is not limited to the context of the practice, information, and charting performed by dentists, but can include anything related to one or more aspects of the mouth or oral treatment, including but not limited to anything related to the practice of dentistry, orthodontics, periodontics, endodontics, prosthodontics, and the like.

In the example shown, system 100 includes one or more client devices 110 on which dental charting information can be accessed, displayed, or modified. In some examples, the client devices 110 can connect to a central device 120. The central device 120 can, in some examples, be a server or electronic database for hosting dental charting information, or can include software applications or modules for performing various aspects of the dental charting system.

For example, a dental office can include several client devices 110 at different locations such as treatment rooms, reception desks, counseling areas, or offices. In some examples, the client devices 110 and central device 120 can be at different locations such as terminals in different offices or a server or database hosted at a remote location. Dental charting or application information can be communicated between devices via network 130. The network 130 can include one or more private and/or public networks. The network 130 can include a wired network such as a wired local area network or the internet, or wireless networks such as cellular telephone networks or Wi-Fi networks.

While the example system shows three client devices and one central device, any number of client or central devices can be used in any suitable arrangement.

In some examples, the central device 120 can host or have access to a database storing dental charting information. In some examples, the central device 120 can provide processing or host an application or software module accessible by a client device for performing various aspects of the methods described herein.

In some examples, the central device 120 itself may also be a client device 110 on which dental charting information can be accessed, displayed or modified.

In some examples, a single electronic device 110 such as a personal computer can be used to store, access, display and modify dental charting information.

In some examples, the system can include a database located at a client device 110, a central device 120, or elsewhere on the network. The database can, in some examples, store dental charting information. In some examples, local or backup copies of dental charting information can be stored at a multiple locations including a client device 110, a central device 120, or elsewhere in the system.

Examples of client 110 and central devices 120 can include, but are not limited to, computers, servers, tablet or mobile computers, or mobile phones.

Figure 2:
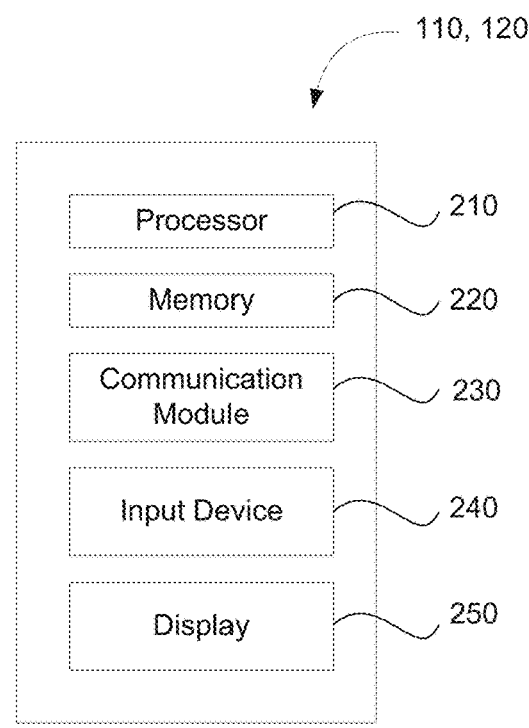
FIG. 2 shows an example client or central device.
Figure 3:
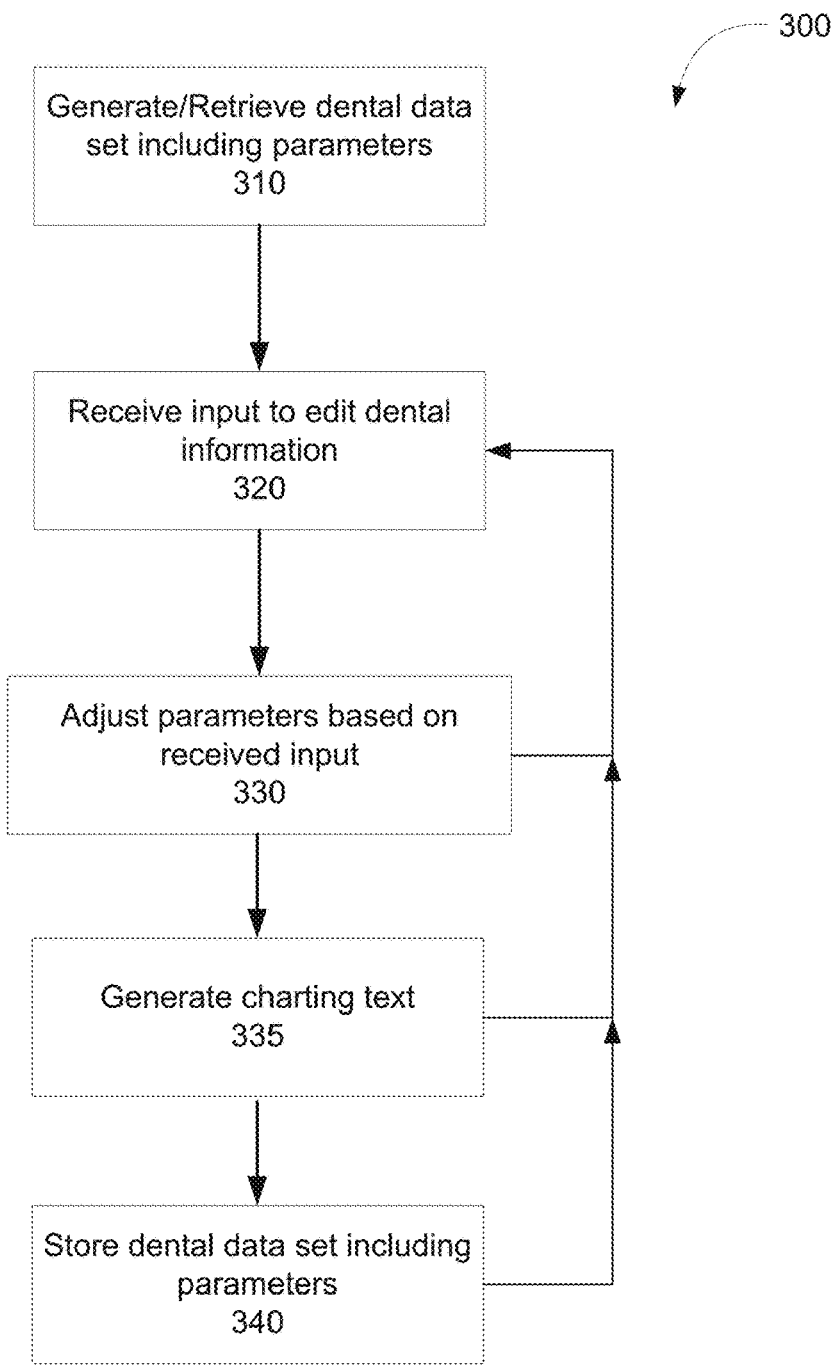
FIGS. 3-6, and 6A show flowcharts illustrating aspects of an example method for charting dental information.

FIG. 2 shows an example client 110 or central device 120. The device 110, 120 can include one or more processors 210 connected to one or more memories 220, communication modules 230, input devices 240, or displays 250. In some examples, a memory 220 can store modules which enable a processor 210 to perform any aspect of the methods described herein. In some examples, a memory 220 can store dental chart information. In some examples, a memory 220 can store models, images, renderings or other visual representations of various anatomical structures or dental appliances.

In some examples, a device 110, 120 can include a communication module 230 which may include hardware or software for communicating dental charting or application information over network 130.

In some examples, a device 110, 120 can include or be connected to one or more input devices 240 for receiving inputs to edit dental information or to otherwise operate the device 110. Input devices can include keyboards, mice, touchscreens, touchpads, navigation devices, remote controls, tablet computers, mobile phones, or other suitable input devices.

In some examples, a device 110, 120 can include or be connected to a display 250 for displaying aspects of a dental chart.

In some examples, computer-readable instructions such as a computer program or application can be installed or otherwise operable on a client or central device, or can be stored on a non-transitory, computer-readable medium.

In some examples, when dental charting information is stored at a central device, it can be accessed by different users at different locations or on different client devices.

In some examples, one or more devices 110, 120 can be configured to request, receive and/or verify user credentials to control access to dental charting information stored in the system 100. In some examples, user credentials or identifiers may be stored in association with additions, deletions, or other modifications performed on a dental charting information.

In some examples, user credentials may be based on a user account at an operating system level, a user account in the dental software application, via a user account in another software application working in conjunction with the current system, or otherwise. The one or more devices 110, 120 may be configured receive input signals representing user credentials for verification before access is granted.

Access may be controlled to the application as a whole, on a dental practice basis, on a dental chart by dental chart basis, or in any other manner.

In some examples, electronic dental charting can reduce or eliminate paper-based records-keeping and possible inefficiencies of searching for, transporting or losing physical records. In some examples, the system can be configured to allow for the printing of paper charts.

In some examples, the system can be configured to allow for the creation and storage of electronic backup copies of the dental charting information.

The system 100, in some examples, provides a digital design environment in which aspects of the system can be used to create and store dental charting information based on parametric models.

In some examples, the system can model dental charting information for any dental procedure, including orthodontic, periodontal, endodontic, pedodontic, medical, and oral-surgical procedures.

In some examples, one or more devices 110, 120 and/or one or more of their processor(s) 210 can be configured to performed any aspect(s) of the methods described herein.

FIGS. 3-6, 6A show flowcharts of example methods 300, 300a, 300b, 300c, 300d of charting dental and/or medical information. These flowcharts show example operating sequences of example system 100; however, it is to be understood that aspects of different flowcharts can be combined or can be performed in any suitable order.

At 310, a device can be configured to generate or retrieve a dental data set. In some examples, the dental data set can be retrieved locally from a memory or another storage connected to the client device 110. In some examples, the dental data set can be retrieved from a central device 120 via network 130.

The dental data set can, in some examples, include a set of separately-modifiable parameters which define information regarding aspects of a state of a patient's dentition or mouth. The parameters can define aspects of one or more objects relative to a base model, for example, the location, size or orientation of a tooth relative to a base model. In some examples, the base model can include a set of rules such as a three-dimensional coordinate system. In some examples, the base model can include one or more two or three-dimensional curves representing the shape of parts of a dental arch. In some examples, the base model can include base markers or base tooth positions on the curve(s). The base model may also include base parameters identifying base object models.

The dental data set, in some examples, can include parameters referring to object models of teeth, implements, gums, restorations, fractures or other objects in a patient's mouth. In some examples, these models can define relative dimensions and boundaries of the object. The models can also, in some examples, define rules of how the object can be scaled, moved, rotated, be attached or interact with other objects. In some examples, models can be stored as part of a software package or a library on a client or central device.

In some examples, the models can include default parameter values. The models themselves can be stored separately from a dental data set and/or the representative parameters.

In some examples, the teeth or other object models can be generic models, or can be models based on actual characteristics of a patient's actual teeth.

In some examples, a dental data set can include parameters identifying or referencing multiple object models and various adjustable aspects of the object. For example, a dental chart can include parameters identifying or referencing a central incisor tooth. The dental data set can, in some examples, include additional parameters defining the location, orientation or other aspects of the incisor relative to a base model. For example, the dental data set can include a parameter identifying a tooth based on the central incisor object model, and parameters specifying the location of the object on a curve representing the patient's maxilla dental arch. In some examples, the data set can include parameters defining characteristics of one or more object models related to a base object characteristics. For example, the data set can include a size or scaling parameter defining the size of a tooth object relative to the base or default size of the tooth object.

The data set can, in some examples, include a collection of parameters or values in a parametric model for defining aspects of a subject dentition/mouth or other anatomical structure.

By referring to object models such as teeth and dental implements and adjusting parameters based on properties of the object models relative to a base model or set of rules, a patient's mouth can, in some examples, be completely represented three dimensionally by a set of parameters. These parameters can provide information for one or more processors to generate signals for displaying a two or 3-dimensional visual representation of at least a portion of a dentition/mouth represented by the data set.

An internal record of all user interactions with the 3D model may be stored by a program. When a user performs a modification to the model, such as adding an orthodontic appliance, the program may store internally the parameter that represents that state. The information stored internally may vary depending on the parameter. This may include (i) the object the parameter is applied to (a single "item" in the 3D model, such as a tooth, a bracket, an archwire, an aligner, which for example may be plastic, clear and/or transparent), and (ii) details regarding that parameter (i.e., the template 'text' used to represent that object, color, etc.).

For example, if the user marks a tooth as an implant, then one of the parameters stored with every tooth object (whether the tooth is an implant or not) may be modified internally in the program to represent the new state of that object.

In another example, if a user marks a filling on a tooth by using a pointing device and selecting the area/surface where the filling will be stored, the program may create parameters representing where that filling was marked. In the case of the filling, this could be 3D model information (i.e., UV coordinates) describing how that filling can be shown in future instances when the user opens the treatment card, without having to click and mark the same filling each time.

The collection of all the parameters, in total, that the program has, may be described as the program's "state." The state may simply describe everything that the user has inputted into the program to date. This may include brackets, archwires, elastics, springs, aligners, fillings, and other dental appliances and procedures.

Figure 4:
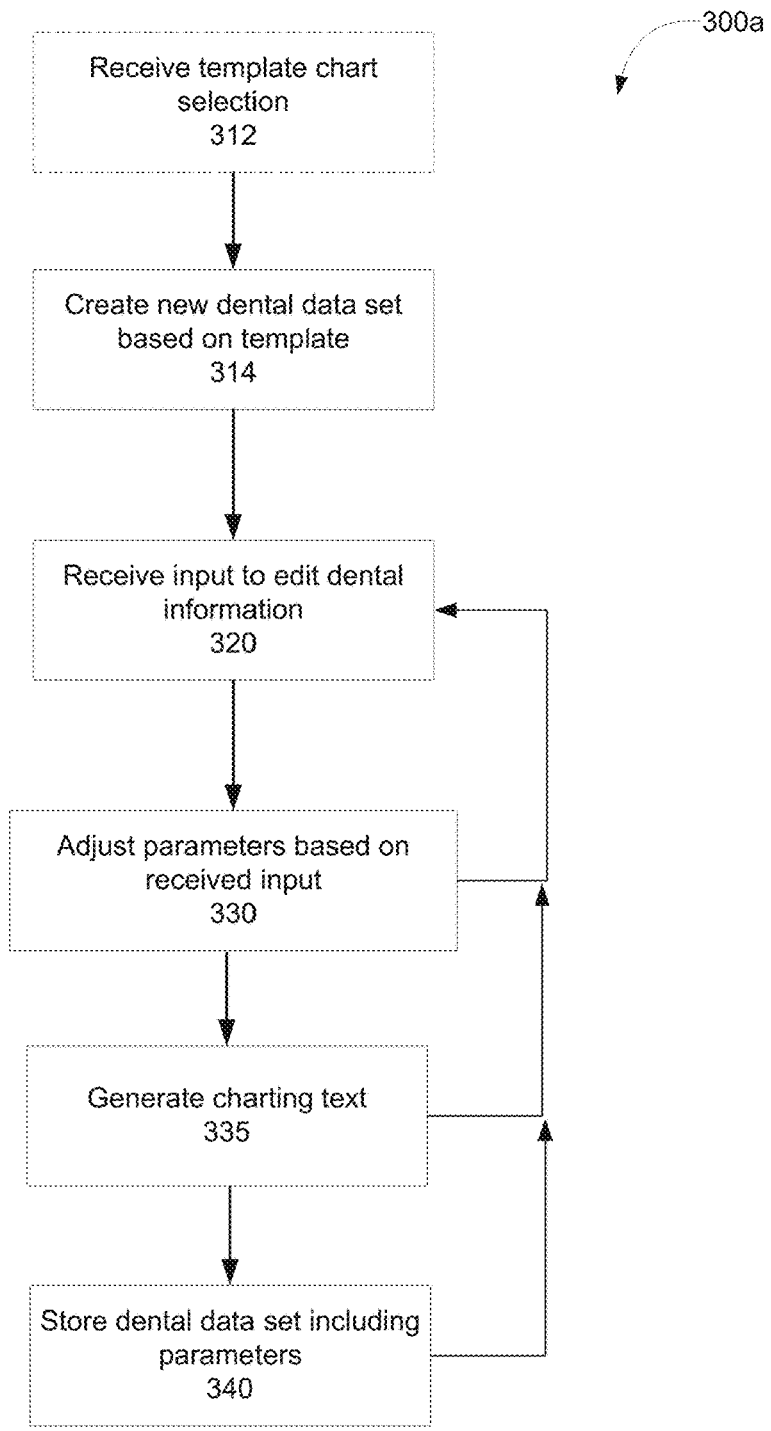
Figure 5:
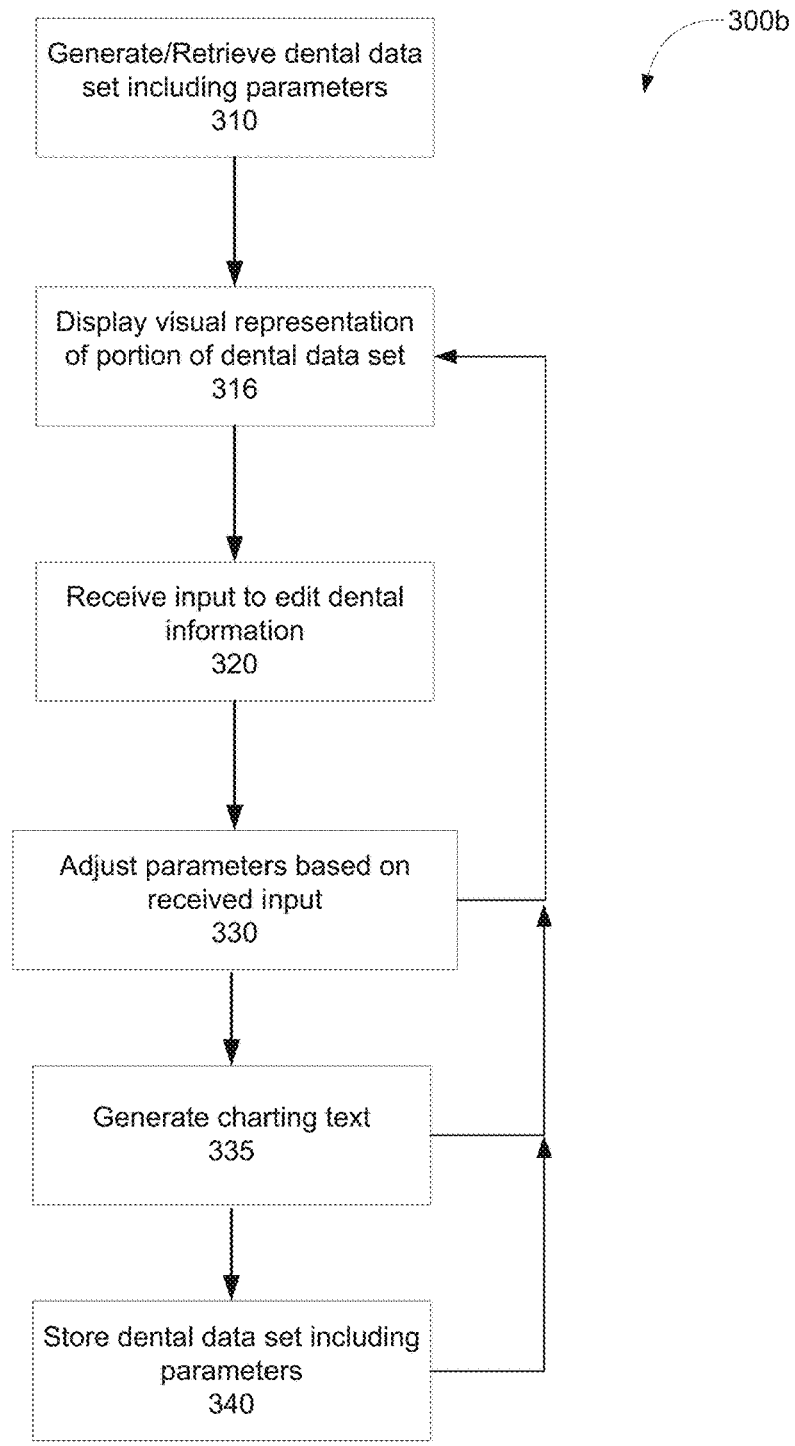

With reference to FIG. 4, in some examples, generating/retrieving (block 310) a dental data set can include retrieving a template dental data set for creating (block 314) a new dental chart. In some examples, the template dental data set can include parameters identifying all aspects of an average mouth. For example, a template dental data set can include parameters defining a standard set of teeth and parameters defined default locations and orientations of those teeth.

In some examples, the template dental data set can be based on a default base model and any parameter can define deviations from this base model.

In other examples, the template dental data set can include parameters defining default locations and orientations of objects relative to a base model such as a three-dimensional coordinate system or one or more curves defining the shape of a dental arch.

In some examples, the system can include different template dental data sets or base models on which a patient's dental data set can be based. For example, there can be different template data sets or base models for primary dentitions (baby teeth) or permanent dentitions (adult teeth). In some examples, the system can have different template data sets or base models which incorporate the different mouth or tooth shapes common to different populations.

When multiple template data sets or base models are available, in some examples, a device can optionally receive (block 312) an input to select the template data set or base model from which a new dental data set is to be created.

In order for software to generate text notes, it may compare at least two separate model states. Typically, this may result from having at least two different patient visits, which may have some parameters which differ. For example, the orthodontist may have switched out one of the archwires.

The software may analyze the at least two separate states, taken from at least two different visits, and may compare them, parameter by parameter, to determine the differences between the at least two visits. The program may convert these differences into a text format. For example, say that on a particular visit, the orthodontist used a wire "a" and the next visit switched to a wire "b". The program may analyze both visits, see this difference, and create a text statement of a predefined format. For example the program may make a notation such as "changed upper archwire from a to b."

Each different parameter may be converted to a text statement. The parameters may differ depending on the object and its relevant information. For example, when an elastic is added, the attachment points it connects to may be stored, along with the elastic type and duration. Periodontal measurements may take the form of six measurements per tooth.

Once the program has gone through all parameters and created the statements, it may combine them into one body of text, and may append header and footer information. The header information may include the date of the visit (the latest of the at least two visits being compared), patient name, etc. The description of the parameters, along with the header/footer, can form documentation that can be used independently of the program. The documentation can describe all relevant information that was input into the system.

This operation of comparing at least two visits for parametric differences can happen on any number of occasions. It may be triggered as soon as a user inputs one change into a visit. The program may determine which visits to compare (the previous visit if there is one, and a base-model if there is no previous visit), and may automatically generate the text description.

In some cases, an existing visit may be reopened and modified. In this case, the program may compare the latest parameters of the existing visit with the previous model of that visit to determine the changes the user made during that visit.

At 316 (FIGS. 5, 6, 6A), one or more processors can be configured for generating signals for displaying, on a display, a visual representation of at least a portion of a dentition represented by the dental data set. In some examples, this visual representation can be updated in real- or near real-time as changes are made to a dental data set and the underlying parameters.

In some examples, displaying the visual representation can include displaying visual representations of objects in a dentition. In some examples, the objects, such as teeth or implements, can be displayed based on the associated parameters in the dental data set. In some examples, the visual representations can include dental conditions, restorations or dental appliances on one or more teeth based on the parameters of the dental data set.

Parameters in the data set can, in some examples, provide information for identifying objects, renderings, images, pre-images or other data for displaying a 3D representation of one or more teeth, appliances, conditions, or other aspects of a mouth or dentition. For example, parameters can identify a specific visual model of a tooth, implant, or other object which can be used to generate signals for displaying a 3D representation of part of all of the subject dentition/mouth.

At 320 (FIGS. 3-6, 6A), a client device receives an input to edit dental information. In some examples, the input can be received when a keyboard input, such as a shortcut key or an entered data value, is received, when a menu option is selected, or in any other manner. In some examples, an input can be received through an interaction with or via an image or visual representation of at least a portion of the dental data set. For example, a user can click and/or drag a cursor, provide keyboard inputs, or touch and swipe a touchscreen, over a tooth to adjust its position or orientation. In some examples, an input to edit dental information can include any one or combination of clicks, gestures, keyboard or shortcut inputs. In some examples, an input can include audio commands.

Receiving an input to edit dental information with or via a visual representation may, in some examples, include receiving an input via a slider, selection box/list or other parametric adjustment interface element.

At 330, 330a parameters included in the dental data set can be adjusted based on the received input. In some examples, by iteratively receiving inputs and adjusting parameters, a dental data set can be updated to document the state of a patient's mouth/dentition.

In some examples, at 335, one or more processors can be configured to generate charting text. While illustrated, for example, in FIGS. 3, 4, 5, and 6A as occurring after the adjustment of parameters, the generation of charting text can also be configured to occur before or concurrently with the adjustment of parameters.

One or more processors may be configured to generate charting text based on the activity associated with the received input. For example, if an input received with/via the 3D representation indicates that an area of tooth decay is to be added to a particular incisor, the one or more processors may be configured to generate a charting entry of "Caries detected on buccal face of 21".

In some examples, the one or more processors may be configured to automatically generate charting text based on template(s) or defined phrases/terminology. These template(s) may be based on standard or generally accepted dental/medical notation/terminology, or in some examples, may be customized based on a practitioner's preference.

As noted in the example above, in some instances, the generated charting text may be less specific than the actual information in the data set. For example, while an area of tooth decay may be specifically defined by way of one or more parameters in the data set in terms of location, size, depth, etc., the generated charting text may only indicate that the caries is detected on a particular face of a particular tooth. In some instances, this may provide simpler, charting information without extraneous details.

In some examples, the one or more processors may be configured to only generate charting text for certain types of inputs. For example, a view change input may not generate charting text.

In some examples, the generating the charting text may include generating text, activity codes, etc. for billing or insurance purposes.

In some of the described example embodiments, the automatic generation of charting text corresponding to an input received via the visual representation may eliminate or reduce the need for a user to manually input charting text. In some examples, this may reduce the time burden on a user.

In some examples, the automatic generation of charting text may reduce errors or charting inconsistencies through its use of standardized language. In some examples, the automatic generation and display of charting text alongside the 3D visualization may provide a visual double-check for a user to verify that the proper dental activity has been inputted.

Figure 41:
FIGS. 41 and 42 show examples of converted dental information.

Other non-exhaustive examples of generated charting text appear in FIG. 41.

In some examples, once a dental or medical data set is received by the program, one or more processors may create and configure an internal binary state of the program, which either allows (editable) or disallows (lock) modifications of the data set as a whole. This locked state may allow all changes to the view to be performed as defined herein or otherwise as well as traversal between data sets, but may not allow any changes of information attached to the data set, parametric or otherwise. This status may be determined by the 'age' of the data set, the time since the initial creation of that data set, as well as the current authenticated user, or other mechanisms. Additional internal binary states controlling modifications may also exist which apply to sections or parts of the data set (specific sets of parametric or other information), and may be determined by mechanisms described herein or otherwise.

Figure 6:
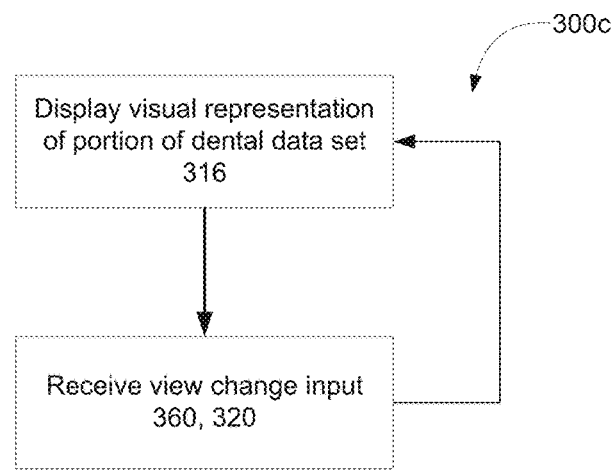
Figure 6A:
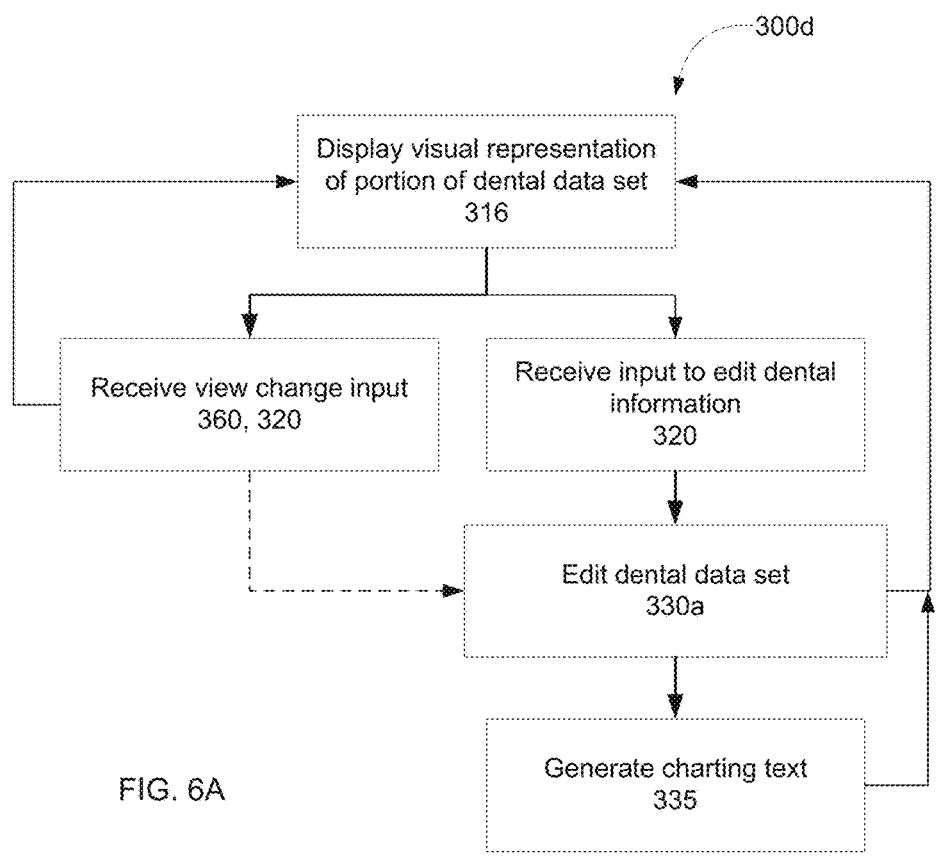
Figure 24:
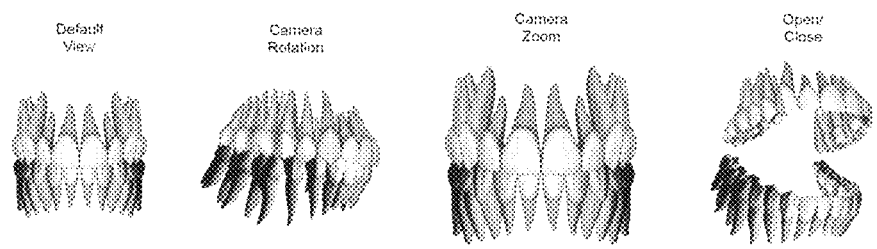

With reference to FIGS. 6, 6A, in some examples, a device can receive 360 a view change input. In some examples, this can include a keyboard command, a menu selection, or interaction with the visual representation. The view change input can represent a request to change a view of the displayed visual representation. Changes to the view can include but are not limited to: repositioning a camera view, zooming in/out, opening or closing the mouth, unfolding the arch, spacing out the dental arches and teeth contained therein, or centering the view on a particular object. FIG. 24 shows example visual representations using a default view, a view after a camera rotation, a zoomed in view, and a view with the mouth open. All changes in view can maintain information contained in the dental arches, using parameters or otherwise, such as attached devices, markings, or objects that create an interconnections between other objects, such as elastics, springs, or c-chains.

In some examples, displaying a 3D visual representation from adjustable views can show restorations which extend beyond a single side of a tooth, or the operation of mechanisms such as (but not limited to) elastics or springs.

By providing a visual representation which can be interacted with to provide an input, the system, in some examples, can provide a user-friendly or intuitive interface for navigating or modifying a dental data set.

Figure 25:
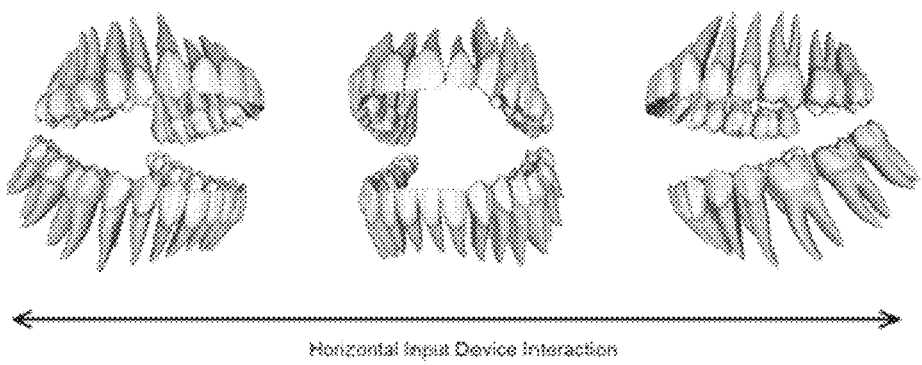
Figure 26:
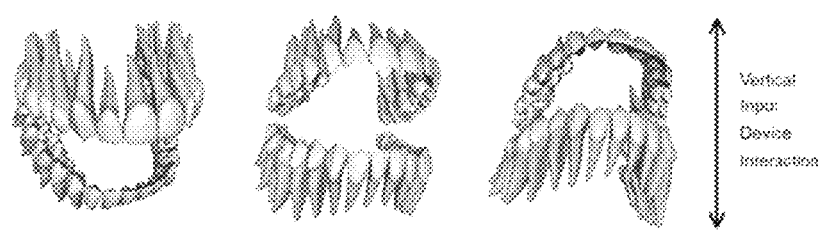

In some examples, the view of the visual representation or simulation can be manipulated through direct simulation interaction when a view change input is received 360. For example, functions can include manipulating the view in the horizontal plane and manipulating the view in the vertical plane. The horizontal view manipulation can be performed by interacting with the input device in the horizontal direction (such as a click-and-drag with a computer mouse, or a hold-and-drag with a tablet pen or finger), causing the simulation to rotate. The rotation can be computed using a linear translation between the amount of pixels the input device moves in the horizontal direction and the angle of rotation. For example, FIG. 25 shows different views as a visual representation is manipulated through direct simulation interaction wherein the input is a horizontal view manipulation. The vertical view manipulation can be determined in a similar way by using the input device along the vertical axis. For example, FIG. 26 shows different views as a visual representation is manipulated through direct simulation interaction wherein the input is a vertical view manipulation. In some examples, the views can be redisplayed in real or substantially real-time as a user continues to hold-and-drag the input.

Figure 27:
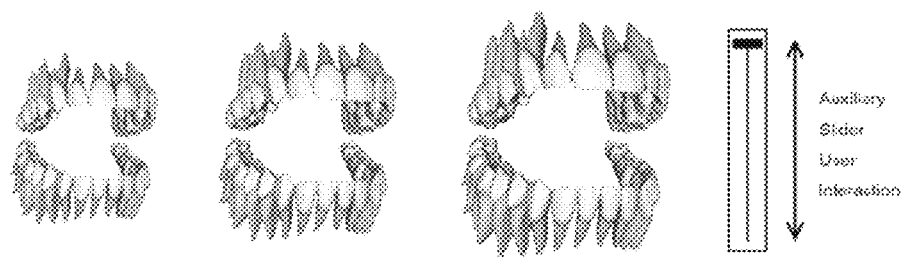

The auxiliary functions for interacting with the view can include zooming, opening/closing the dental arches, and centering the view on a particular object. In some examples, these can be performed using an auxiliary slider provided as part of the graphical user interface of the program, as well as auxiliary functions attached to the input device (such as using the mouse scroll-wheel). For example, FIG. 27 shows different views as a visual representation is manipulated wherein the input is a zoom input.

Figure 33B:
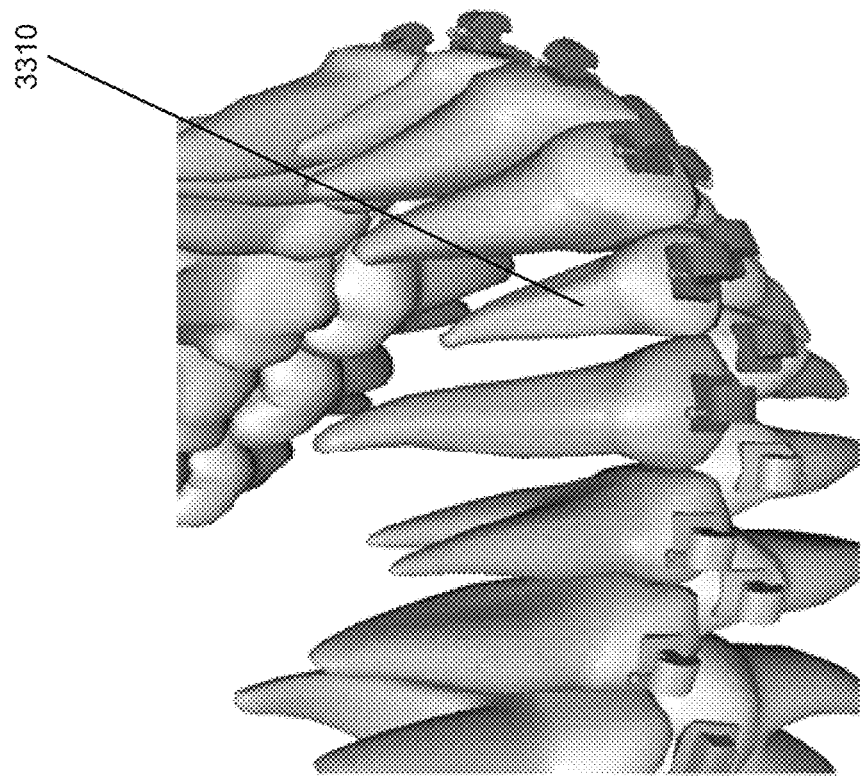
Figure 33A:
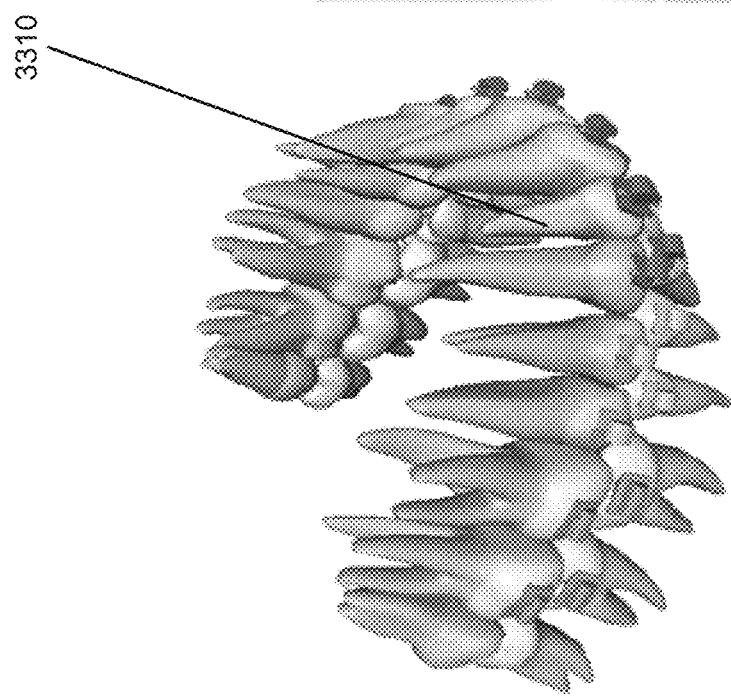

FIGS. 33A and 33B illustrate an example of centering a view on a particular object, wherein an interaction with tooth 3310 in the initial view shown in FIG. 33A causes the view to change to center on the tooth 3310 as shown in FIG. 33B.

Figure 28:
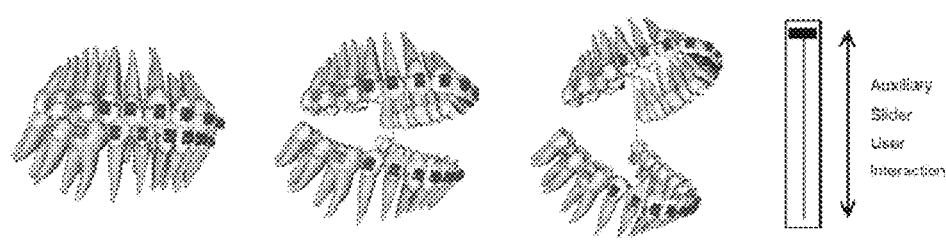
Figure 29:
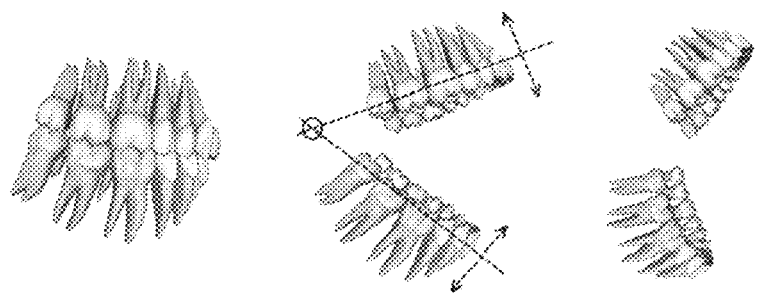

In some examples, the opening or closing of the dental arches can also be controlled via an auxiliary slider, and can perform two separate rotations, one on the maxillary and one on the mandible. Based on the parametrics or otherwise, information for the dental arches, including attached devices and markings, can remain fixed to the dental arches (see for example, FIG. 28). The rotation can be performed about a point located behind the dental arches in space, such that when the arches are opened, the visual representation can show the inside surfaces of the arches (see FIG. 29). In some examples, responding to input to open or close the dental arches can provide a simulation of how the jaws of the dental data set interact or move relative to one another.

Figure 34:
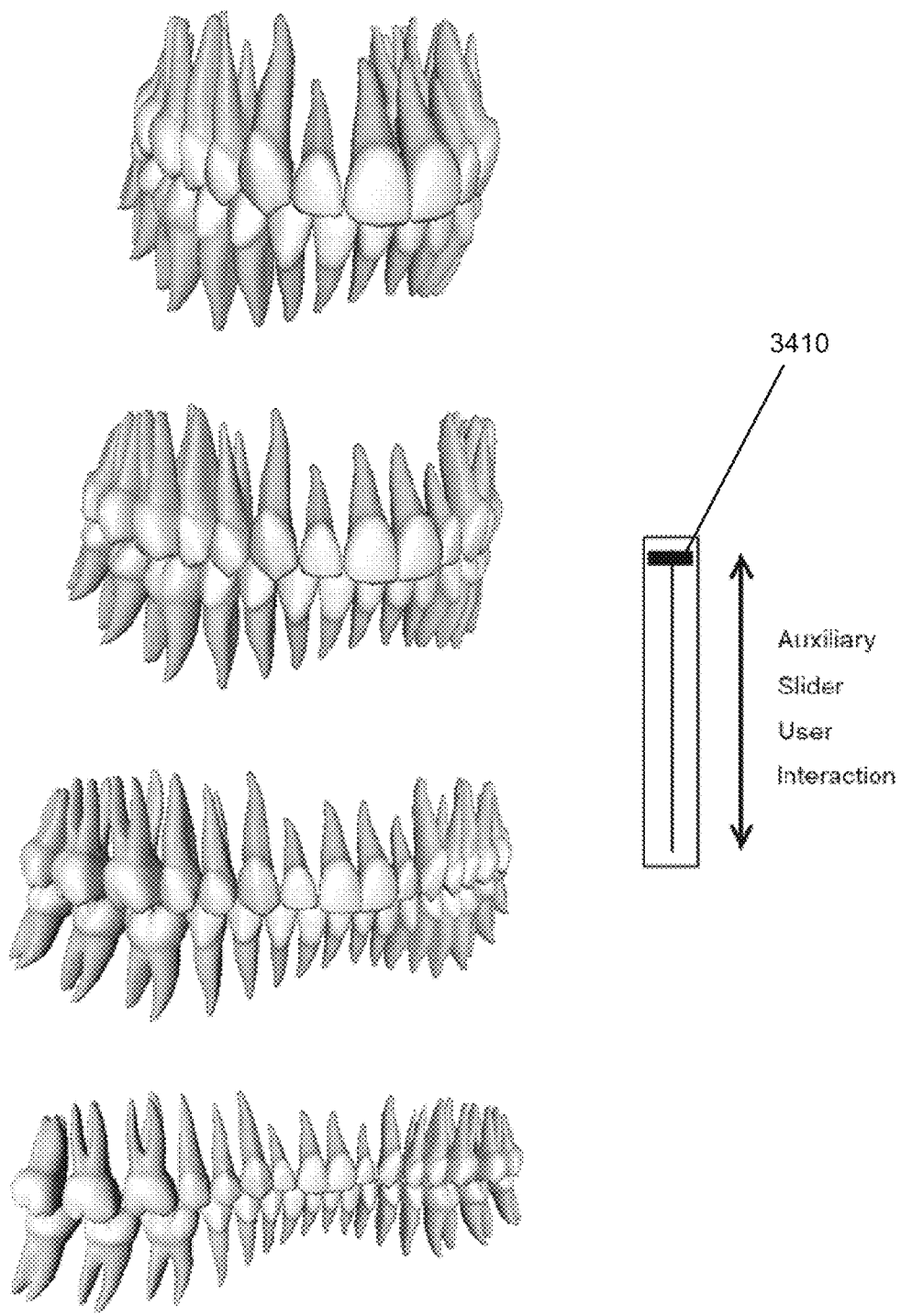

In some examples, the teeth which lie on the arches can be transformed, using a systematic combination of translations and rotations, such that a more desirable view of all individual objects in the data set is attained. This may include a 'folding' operation, where the teeth of the arches are transformed until they lie along a straight line, and the buccal or lingual side of each tooth in the arch is visible without further view manipulation. This transformation may be applied incrementally through interaction with the view, for example, through the use of an auxiliary slider, which can be modified using input methods as described above, as well as inversely. For example, FIG. 34 shows progressive views of a folding/unfolding operation. As the slider 3410 is adjusted, the objects in the view are progressively folded/unfolded.

Figure 35:
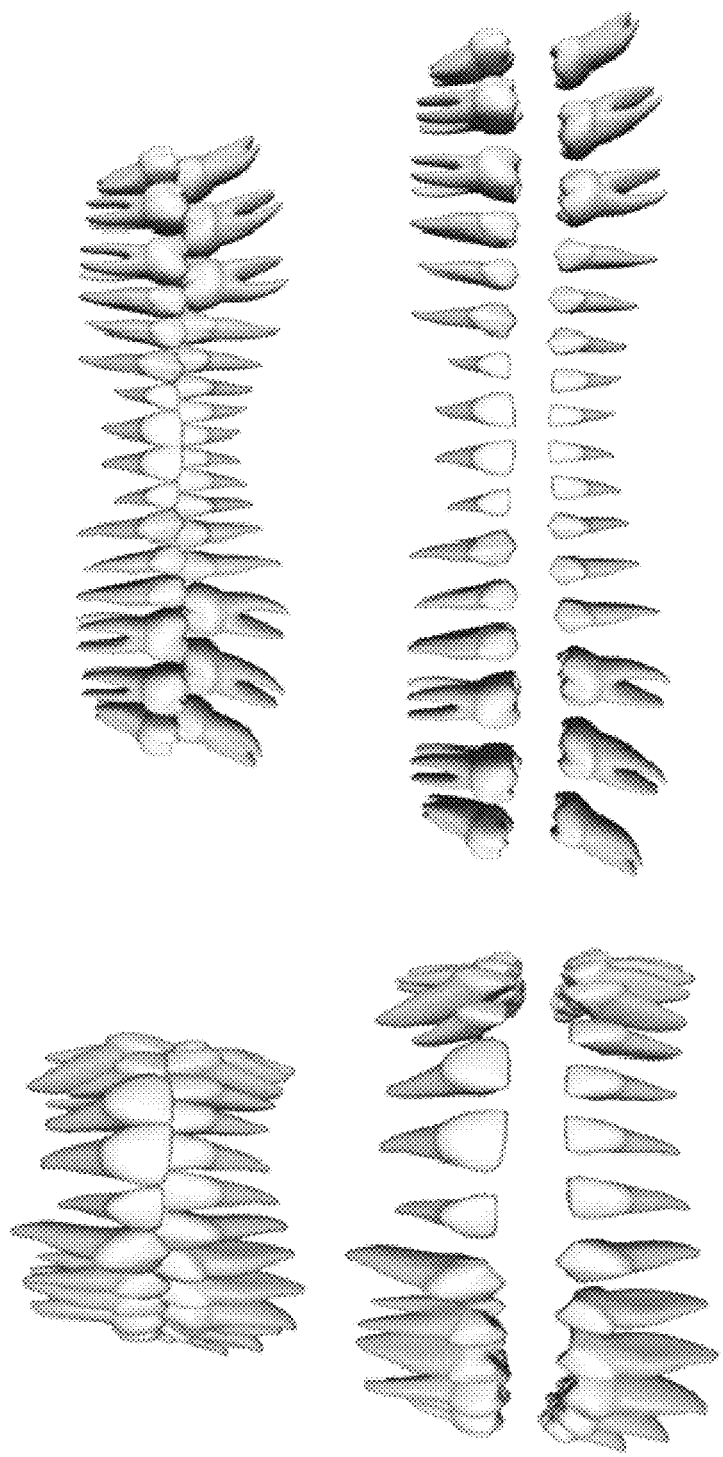

In other examples, interaction with the visual representation or otherwise can cause a variable amount of space to be added between the teeth of the visual representation, such that the mesial or distal sides of the teeth can more easily be viewed or marked. For example, FIG. 35 shows this operation applied to the folded and unfolded dental arches. The operation may have two parameters, which may be adjusted by the user: the equidistance created between each tooth within an arch, and the distance created between the arches.

In some examples, upon receipt of a view change input, one or more processors can be configured to edit view parameters in the dental data set. These parameters may include but are not limited to one or more fold parameters, spacing parameters, angle parameters, and zoom parameters.

In addition to changing the view of a visual representation of a dental data set, inputs to edit dental information can be received 320 via direct interaction with the visual representation, or by other means. In some examples, this can result in real or near-real time editing 330a, 330 of dental data set information by way of adjusting parameters or otherwise. In some examples, as an input is dragged, the visual representation can be updated to reflect the changing dental information. In some examples, as an input is dragged, the visual representation can reflect a proposed change in the dental information until the click-and-drag or hold-and-drag is released, at which point the change to the dental data set can be performed.

In addition to the above, additional examples of receiving inputs, adjusting parameters and generating dental charting information are described for various example dental objects below.

In some examples, a client device can receive an input when a user selects one option from a set of parametric options. For example, a user can document incorrect tooth alignment (a malocclusion) by moving any tooth away from an initial location. In some examples, the initial location can be a default, template or previously defined location. The amount and granularity of displacements can, in some examples, be limited by the system. For example, a system may permit tooth translations in 0.1 or more mm increments, or may limit a maximum tooth displacement from an initial location in any one direction to 1 cm. In some examples, the system can include parameters to identify up to 3 object translations. The translations can, in some examples, be parametrically defined along the axes of the tooth: the mesial-distal, apical-coronal, and buccal-lingual axes. In some examples, parameters can identify object rotations. In some examples these rotations may be defined with respect to the same three axes of a tooth. In some examples, the rotation parameters can also be limited in terms of their granularity (for example, 2.5° increments) or their maximum rotation from a default value (for, example up to 15°).

Figure 7A:
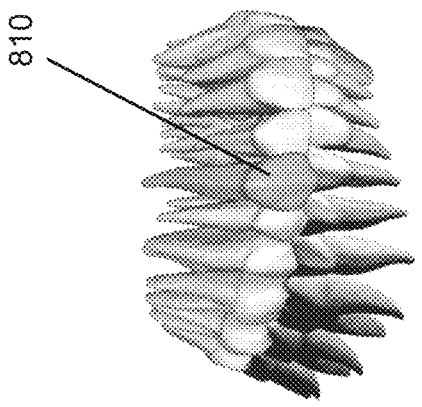
Figure 7B:
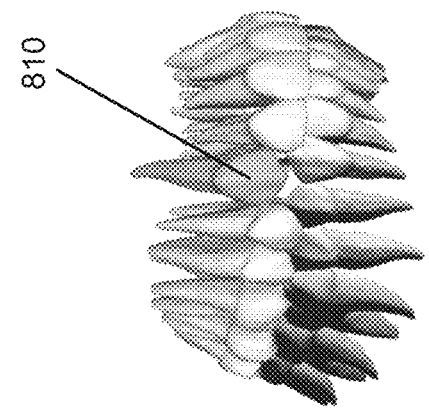
Figure 7C:
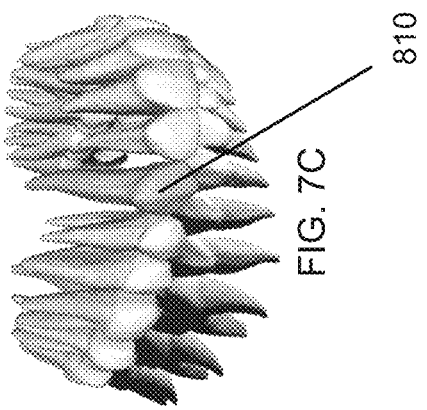
Figure 7D:
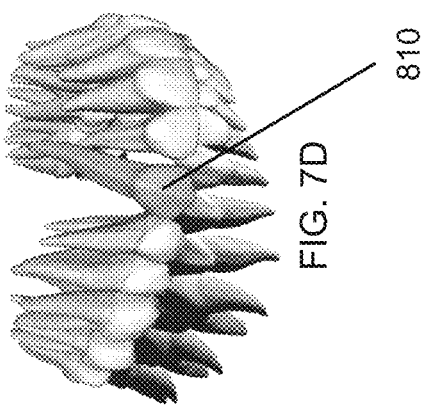

In some examples, translations or rotations can be applied singly, or in combination to a single tooth thereby adjusting one or more parameters. FIGS. 7A and 7B illustrate example before and after visual representations of a tooth 810 before and after a single-dimensional translation. FIGS. 7C and 7D illustrate example before and after visual representations of a tooth 810 before and after a single-dimensional rotation. In some examples, multiple translations and/or rotations can be effected by a single input. For example, a tooth can be translated in two dimensions with a single dragging motion.

In some examples, an input to edit dental information can affect parameters of a single object as seen for example in FIGS. 7A-D. In some examples, an input to edit dental information can affect parameters for multiple objects.

Figure 8:
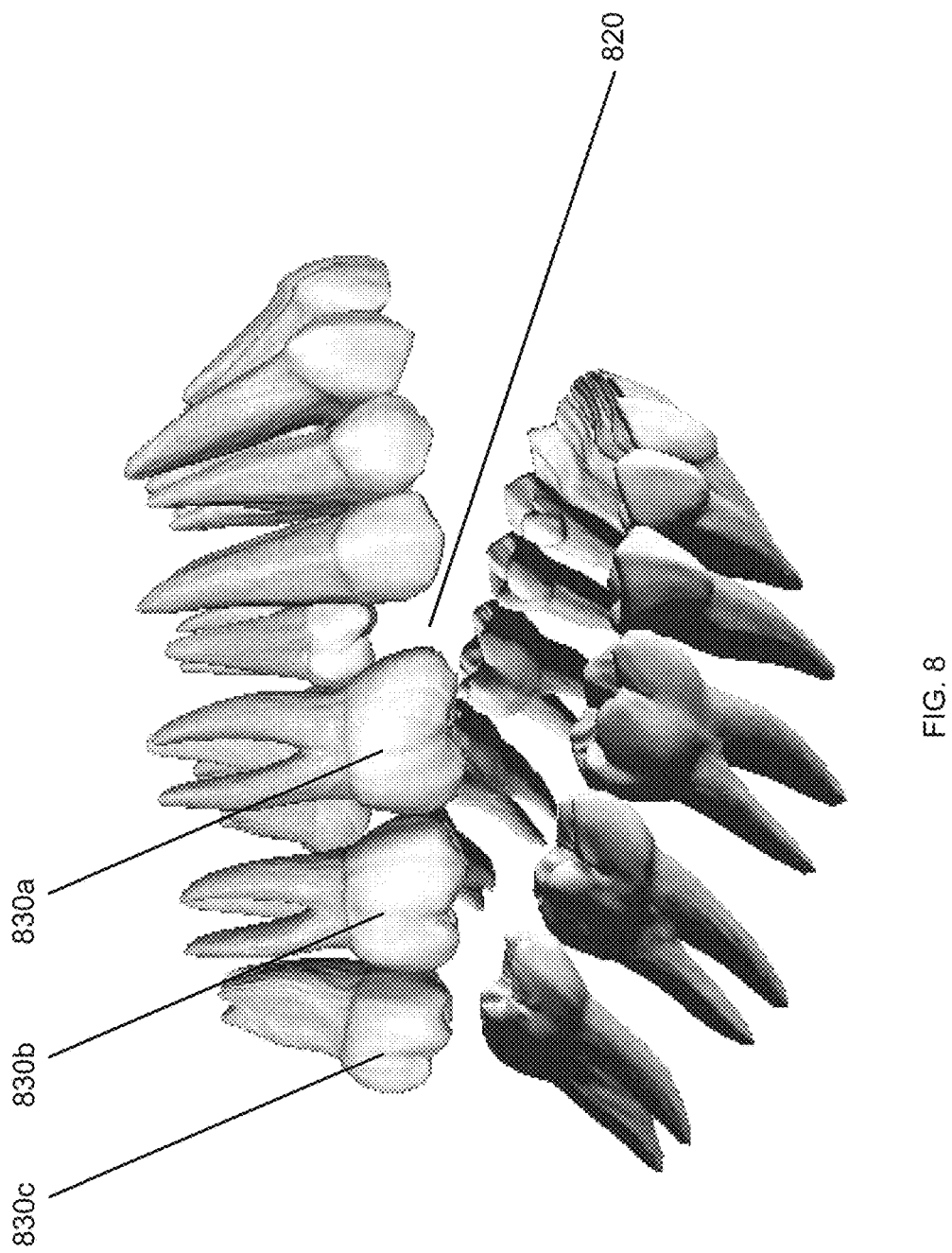

For example, as illustrated in the example visual representation of a dental data set in FIG. 8, a mesial-distal translation can create a space of open contact 820 between teeth. In one example, this space can be defined by the explicit selection of all three upper molars 830a, 830b, 830c and receipt of an input to move the selected teeth. In this example, transformations can be applied to multiple objects.

In another example, the space of open contact 820 can be defined when an input is received to move the single first molar 830a distally. Based on collision detection, the second 830b and third 830c molars can have their location parameters adjusted in conjunction with the location parameters of the first molar 830a.

In some examples, collision detection can be configured to restrict the movement of an object if it would cause a collision or overlap with a neighboring object.

In some examples, when creating malocclusions, real-time collision detection can align teeth in the model according to their physical constraints, such that no unintended gaps or tooth overlaps appear in the model.

In some examples, a received input can result in the adjustment of the parameters of multiple objects or of parameters related to the dental data set as a whole. For example, when a dental data set is first created or after it has already been modified, the initial template used as the base model for the simulation can be modified to better match the patient's dentition. For example, adjustments can be made to the width of the dental arch, the size of the jaw, or the curve of spee (a vertical curvature of the dental arch). In some examples, these modifications can be restricted to a finite set of options. For example, the dental arch can be made wider or narrower, and in some examples can be limited to options between 70% and 130% of the default dental arch width, in 5% increments. In another example, the jaw can be made smaller or larger, and in some examples can be limited to options 70% and 130% of the default dental arch size, in 5% increments. In some examples, differences in jaw size can be displayed as a difference in the size of all the teeth of the dental arch. In another examples, the curve of spee can be set in millimeters, and in some examples can be limited from −5 mm (a downward curvature) to +5 mm (an upward curvature), in 1 mm increments.

Examples of these modifications are illustrated in FIGS. 13A-D wherein FIG. 13A shows an example default or template visual representation of a dental data set, FIG. 13B shows an example visual representation of a jaw with a 15% size increase, FIG. 13C shows an example visual representation of an arch with a 15% smaller width, and FIG. 13D shows a visual representation of an arch with +3 mm curve of spee.

Figure 9:
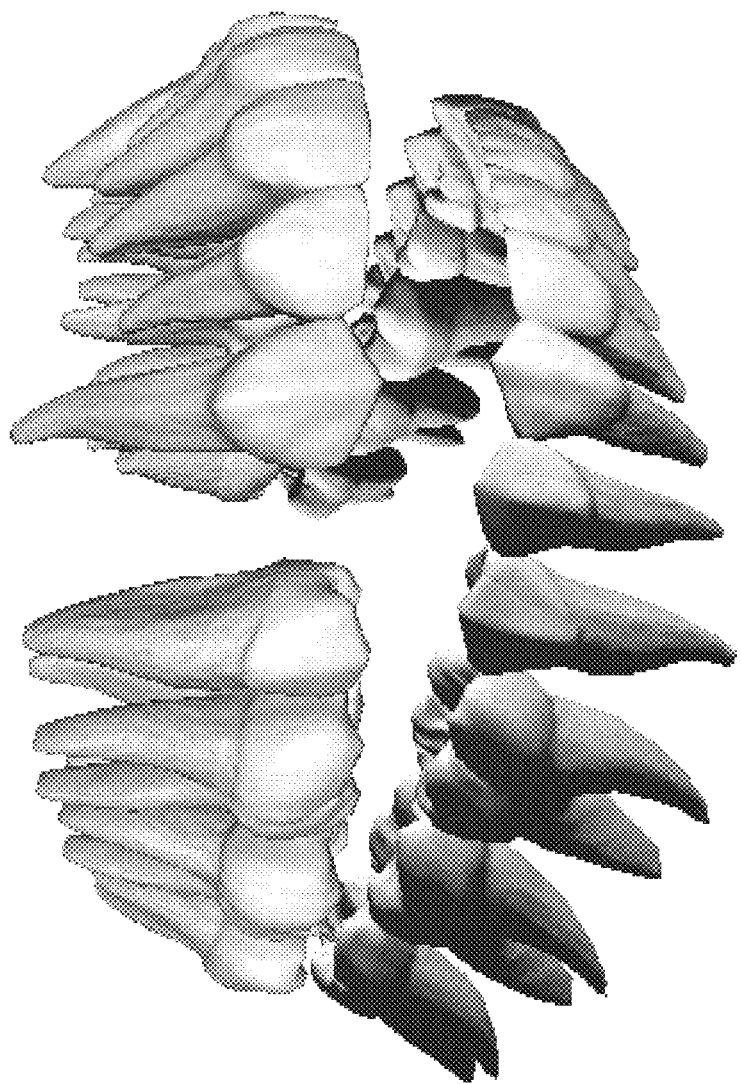

The system, in some examples, can provide other parametric options, such as tooth removal (see, for example, FIG. 9).

Figure 10:
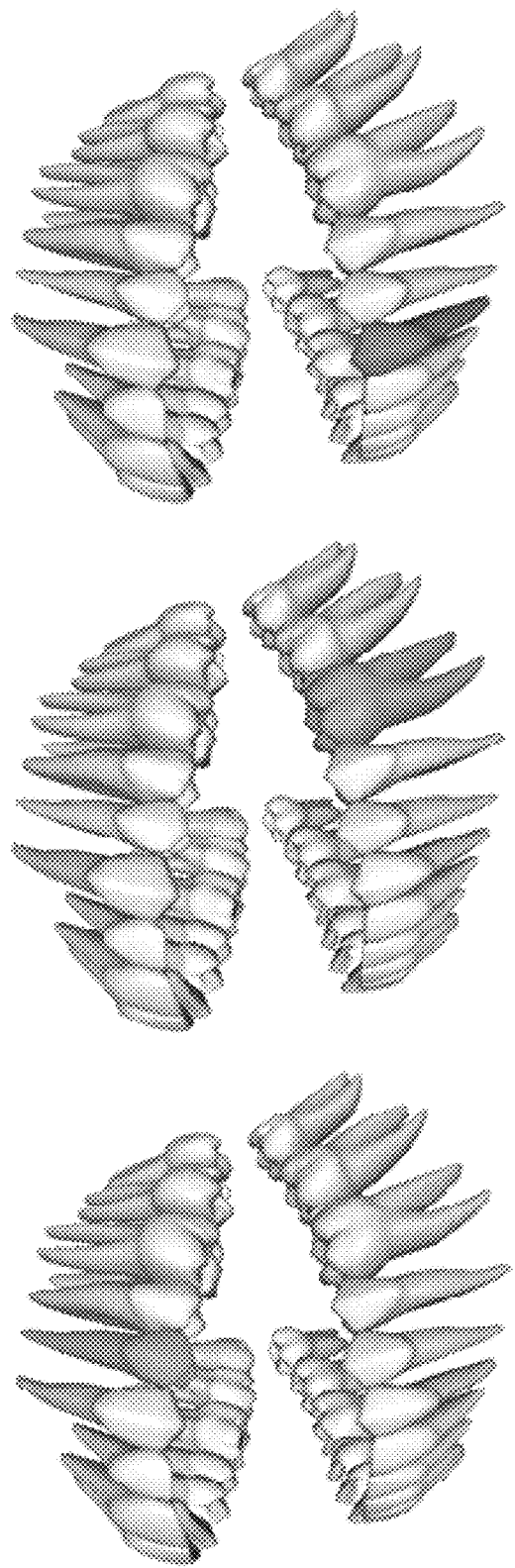

In some examples, a dental data set and the associated parameters can designate the presence of a dental veneer or crown, as well as other conditions (see FIG. 10). In some examples, these parameters can be represented in a visual representation by different colors. The colors, in some examples, can be customized so that a dental office or user may use their own colors to designate what they deem important, and new colors and presets may be added if required.

Figure 11:
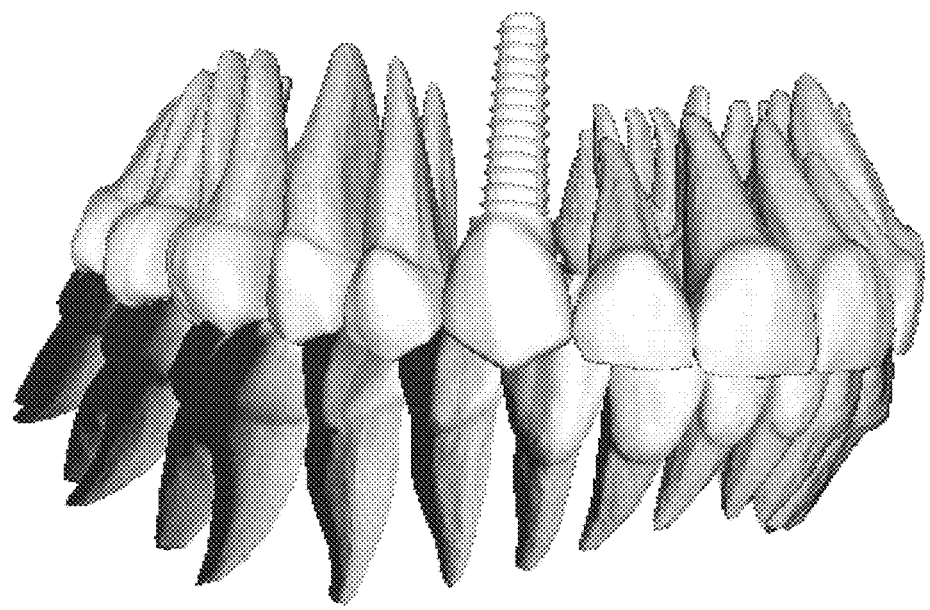

In some examples, parameters can be adjusted to replace individual teeth with an implant (see, for example, FIG. 11).

Figure 12:
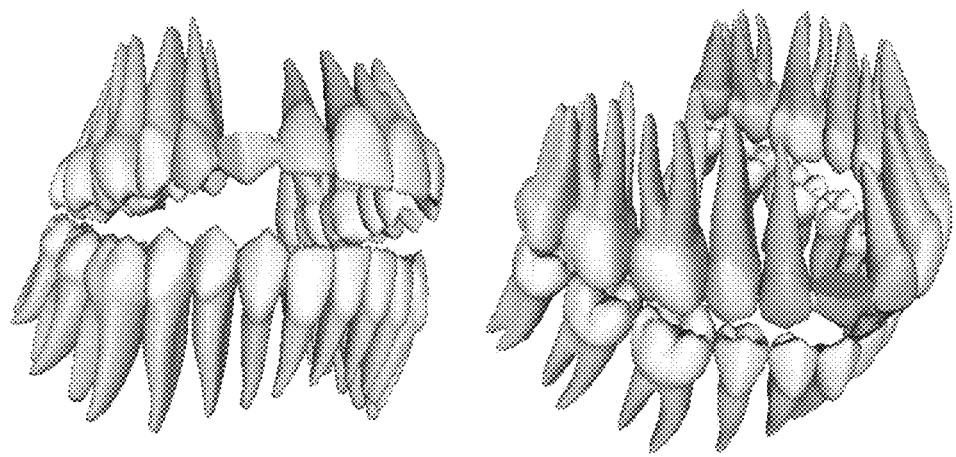
Figures 15A, 15B, 15C, 15D:
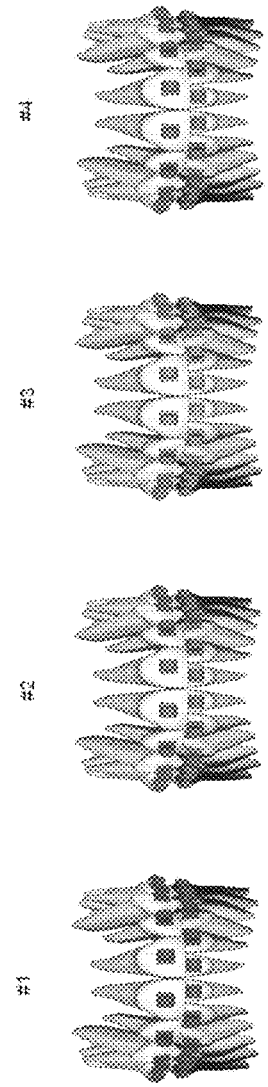

In another example, parameters can be adjusted such that three consecutive teeth which have not been removed can be replaced with a dental bridge. FIG. 12 illustrates two views showing an example of a dental bridge applied to the upper canine.

Parameters or parametric options described herein can be applied to any individual tooth or to any combination of teeth. In some examples, a user can cycle over each tooth the user wishes to modify, select it, and select the appropriate option (such as to change the tooth to an implant, to remove it, or to color-code it). Upon receiving this input, the device can adjust (add, modify, or remove) the appropriate parameters.

Other example parametric options can include adding and selecting orthodontic wires, brackets, elastics, springs, c-chains, aligners, or other implements. Upon receiving an input to add or modify an object such as, for example, an implement, appliance, tooth, periodontal anatomy, dental condition, or restoration, parameters in the dental data set can be adjusted by creating or modifying parameters corresponding to object models or parameters associated with those objects.

For wires such as orthodontic wires, a user can select, for example, different wire thicknesses, rectangular, round, or other cross-sections, different materials, and other wire parameters. In some examples, the parametric sets for these objects are not fixed and can be customizable, for example, to the types of wires, brackets or aligners used by a particular dental office.

Figure 36:
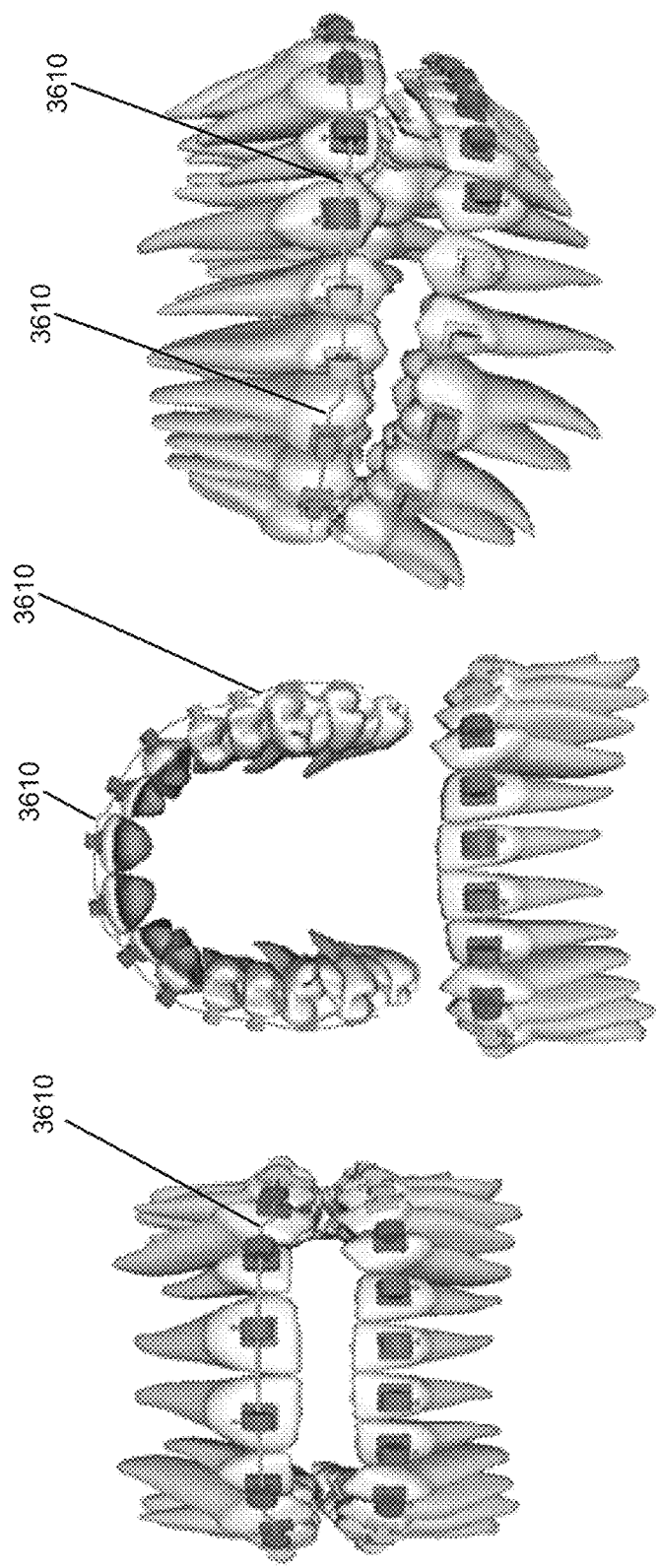
Figure 37:
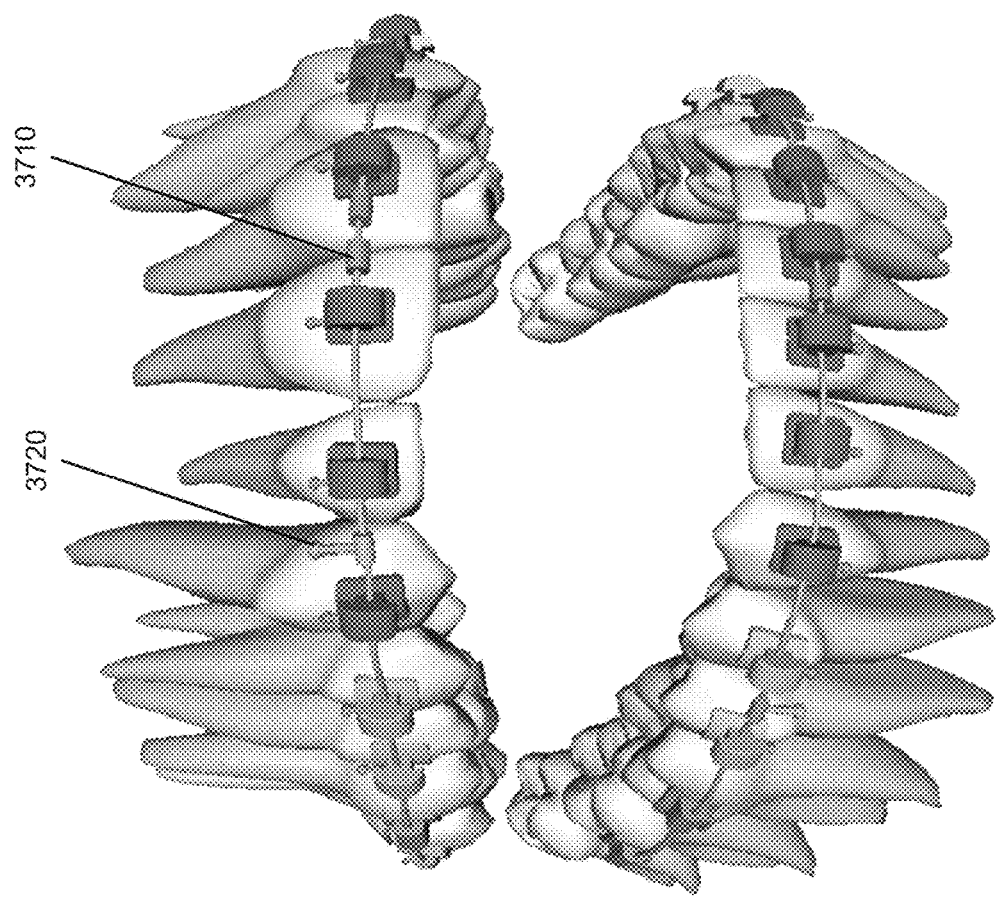

In some examples, a wire can be displayed based on the wire object's parameters. For example, FIG. 14A shows an example visual representation having rectangular wires, and FIG. 14B shows an example visual representation having round wires. The wire object's parameters may also include parameters which describe the existence of wire bends, including their location and effect on the wire. The bend may be located on a wire segment between any two adjacent brackets. The effect of the bend may be a translative effect, where the teeth affected by the bend are moved along any one of or a combination of the mesial/distal or buccal/lingual axes relative to their base positions. The effect may also be a rotation, creating a 'tip' or the tooth or teeth affected, such as toward or away from the mesial, along the wire, where the tooth tips along or away from the lingual, or a rotation along the long axis of the tooth. The bends may be applied to a single tooth or to multiple, as a single bend or as combinations. For example, FIG. 36 shows bends 3610 applied to several teeth of the upper arch. The displacement distance created by the bends may be 1 mm by default, and can be modified by the user. Wire parameters may also include archwire stops 3710 and archwire hooks 3720 as in FIG. 37, as well as the location of the wire, buccal or lingual.

In some examples, a wire can be added to each dental arch, the maxilla and mandible, separately. Color-coding can be used for wires, to allow the operator to distinguish the material and type of wire. In some examples, the colors available, and the type of wire they correspond to, may be customized. In some examples, by default, the wire extends to the furthest brackets that have been applied to each dental arch, but this may be modified by the operator.

In another example, selecting between different types of brackets will render them in different colors, according to the customizable preferences available. In some examples, this color-coding can help dental assistants differentiate between different brackets, such as the type (for example, brand and model) or torque rating of the bracket. FIGS. 15A-D illustrate example visual representations.

In some examples, brackets can be applied to the entire dental arch as a single input preset (such as a standard bracket type applied to the incisors, canines, and first and second molars), or they can be applied selectively to each tooth as required.

In some examples, brackets can be applied to one or multiple selected teeth using a single input.

Figure 30:
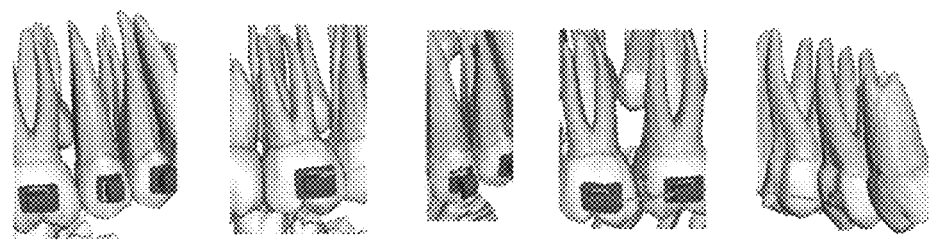

In some examples, orthodontic elastics can be added to the dental data set. In order to add elastics, the user can activate an 'add elastic' function from a menu, and can select elastic attachment objects in the sequence in which the elastic connection is to be applied. The selection can be received from an input device such as a direct interaction with a 3D object in the visual representation. In some examples, an elastic may only be attached to specific types of objects such as orthodontic brackets, orthodontic bracket hooks, wire hooks, and lingual buttons. FIG. 30 shows examples of elastics attached to different types of objects. In another example, wire connections can be similarly inputted through sequential selection of attachment objects.

Figure 31:
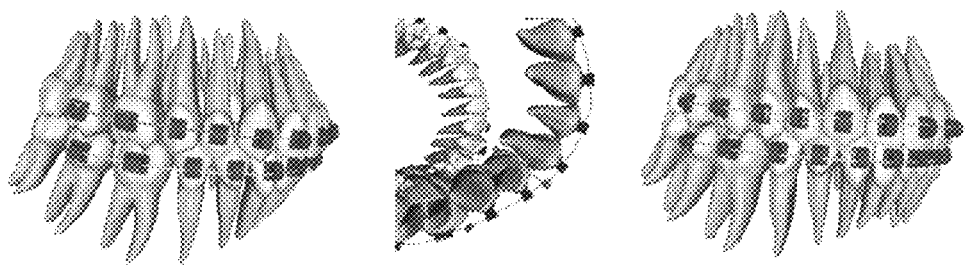
Figure 32:
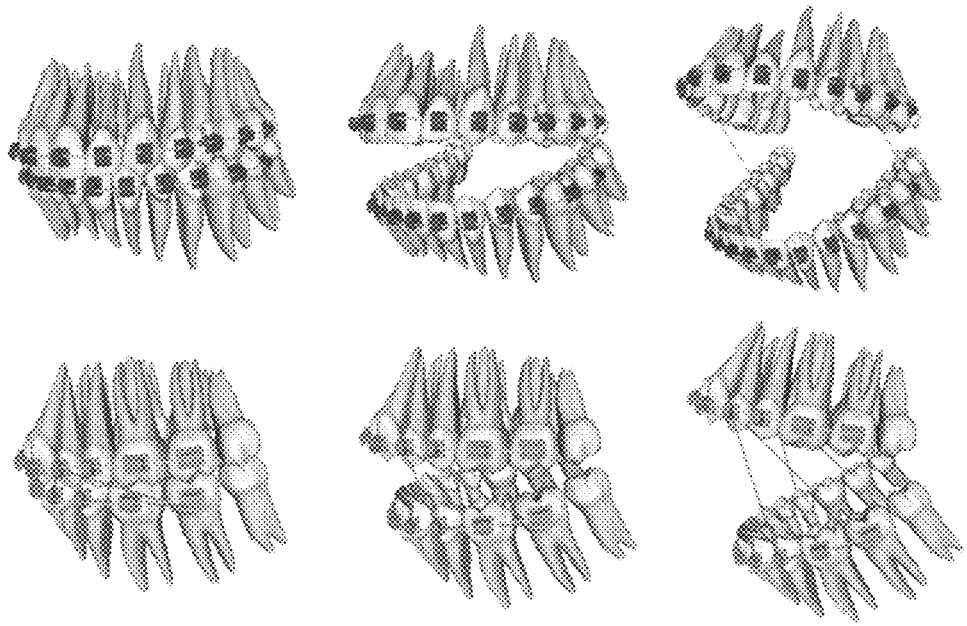

In some examples, the system can render a visual representation including connections between the elastic attachment objects by drawing an outline around the attachment object, and drawing a straight line between the center points of each two consecutive attachment objects (see, for example, FIG. 31). The color of the elastic outlines and lines and textures can be modified by the user and stored as a preference, to represent different types of elastics (such as full-time or night-time, or different types of materials). Opening or closing the dental arch can maintain the connections between the attachment objects to simulate a 'stretch' of the elastic (see, for example, FIG. 32).

Elastics can, in some examples, be added by having the operator select the attachment objects in order, followed by a termination signal which triggers the input. Attachment objects for elastics can include for example, brackets, bracket hooks, wire hooks, temporary anchorage devices and lingual buttons. In some examples, the order in which the operator selects the attachment objects can determine how they are connected with the elastic.

Figure 16:
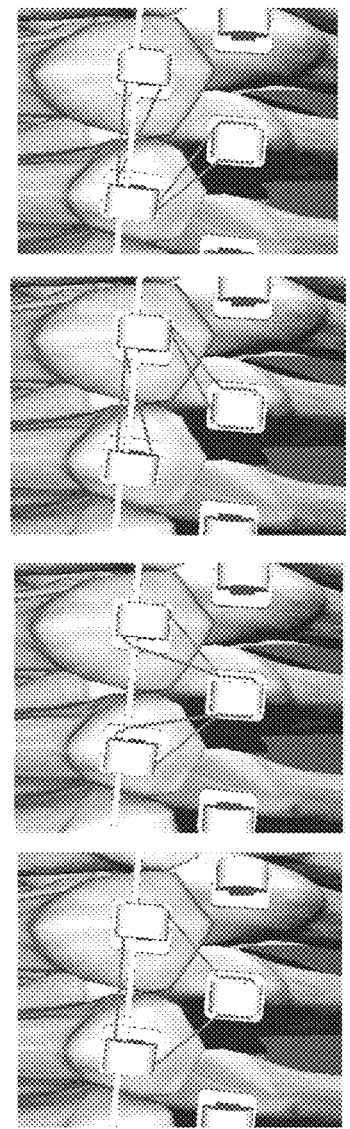

In one example, the operator can pick the attachment objects using a left-click of the mouse, followed by a right-click to designate the end of the sequence. In some examples, the system can differentiate between different elastics, such as full-time or night-time elastics, as well as the material. One or more elastics can be applied, and in some examples, they may connect attachment objects that are located on the same dental arch, or on opposing dental arches. When attachment objects of opposing dental arches are connected, the visual representation can, in some examples, show the elastic stretch as the dental arch is opened or closed. Examples of visual representations of different elastic configurations are illustrated in FIG. 16.

In some examples, elastics may be added by using pre-configured templates. These templates may include the duration and material of the elastic, as well as the configuration of the elastic, defining the attachment objects and their order. These templates may include configurations which are commonly used in the orthodontic profession, such as Class II, Class III, triangle, or other, and may be customized. In some examples, the user may add the template without needing to specifically identify the material and attachment objects of the elastic, but which may be modified after the fact.

Figure 38:
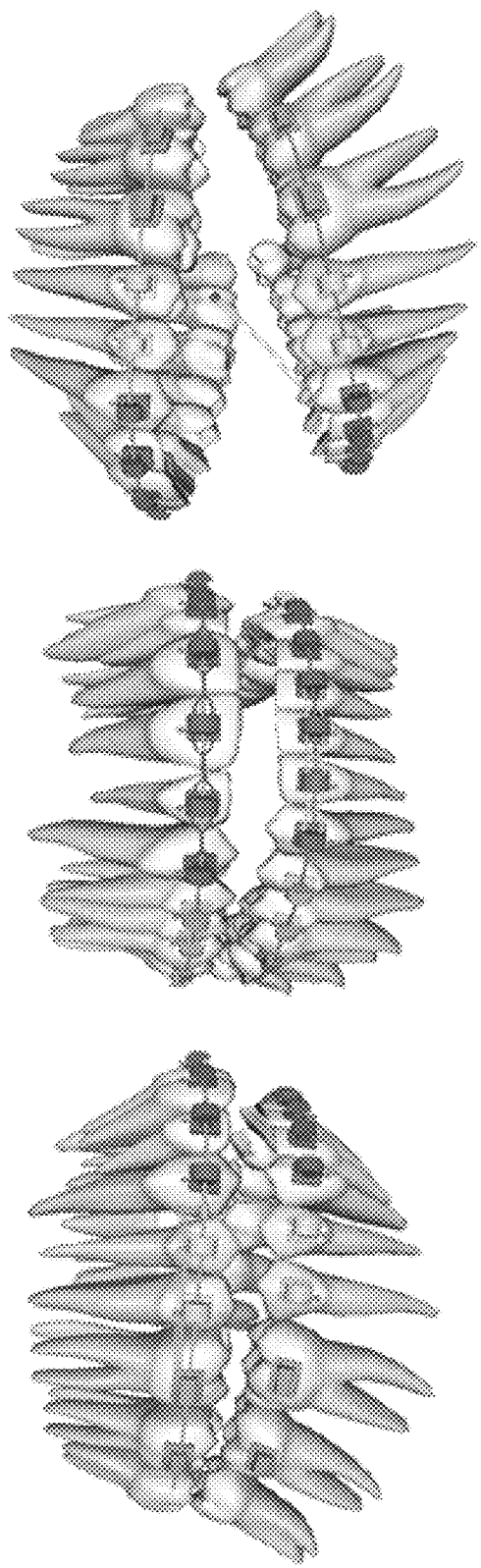

In some examples, other types of objects which create an interconnectedness between attachment objects may be added, such as springs and c-chains. These objects may be attached to specific marking points of other objects, including archwire hooks, bracket hooks, bracket bodies, lingual buttons, and temporary anchorage devices. For example, FIG. 38 shows some of these objects. C-chains may include parameters which specify whether they are open or closed, and when attached to bracket bodies, may be over or under the wire.

Figure 17:
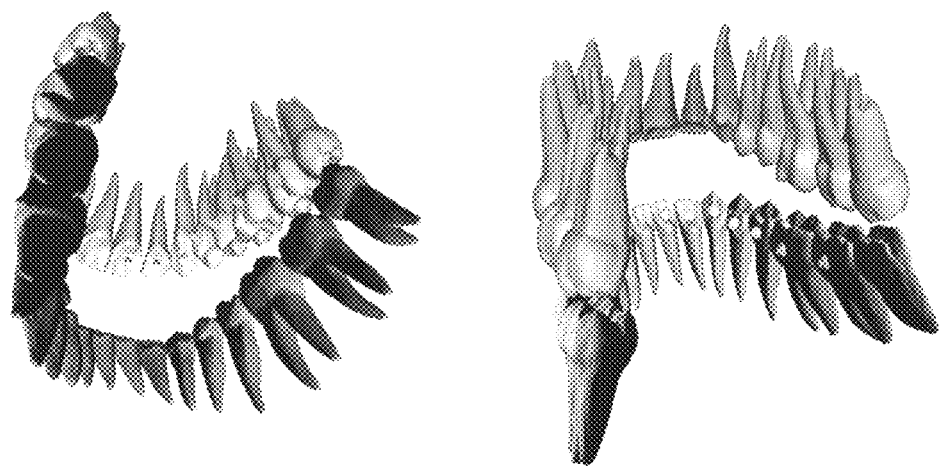

In another example, lingual buttons and bite turbos can be added to any single tooth, or any combination of teeth. Example bite turbos and lingual buttons are illustrated in the example visual representations of FIG. 17.

In some examples, springs may be added to any wire segment (a 'piece' of wire that is located between any two adjacent brackets). Applied springs can, in some examples, be designated as closed springs or open springs, and can be added to one or more wire segments. Any wire segment can be used. In some examples, an archwire stop may also be added to any wire segment.

In some embodiments, one or more appliances defined by the dental data set can include one or more parameters and/or modifiers for defining one or more aligners. An aligner, in some examples, can include an appliance configured for fitting over or otherwise overlaying two or more teeth to impart force on the teeth for straightening, twisting or otherwise moving the underlying teeth. In some examples, the aligner(s) may be clear, transparent or are otherwise such that the teeth underlying the aligner are visible.

In some embodiments, the dental data set can include a set of base parameters including object identifiers identifying different portions of an aligner. In some examples, aligner portions can be defined or separated on a tooth-by-tooth basis. In other words, each aligner portion may correspond to a particular tooth. In other embodiments, aligner portions may not correspond to a tooth on a one-to-one basis or may define portions of an aligner which overlie portions of a tooth.

In some embodiments, the parameters and modifiers associated with an aligner portion can be based on or dependent on the underlying tooth. For example, an aligner portion can be defined to have a shape, orientation and/or position such that it overlays the corresponding underlying tooth.

In some examples, the parameters and/or modifiers for an aligner portion may be linked or otherwise dependent on the parameters and/or modifiers of the corresponding tooth. When an input to change a modifier for a particular tooth, in some examples, the processor(s) can be configured to adjust at least one modifier associated with an aligner portion corresponding to the tooth. In some examples, the aligner portion may be defined relative to a tooth, so changes to a tooth parameter or modifier may automatically result in a change to the visual representation of the corresponding aligner portion without changing any aligner portion parameters and/or modifiers.

Figure 46:
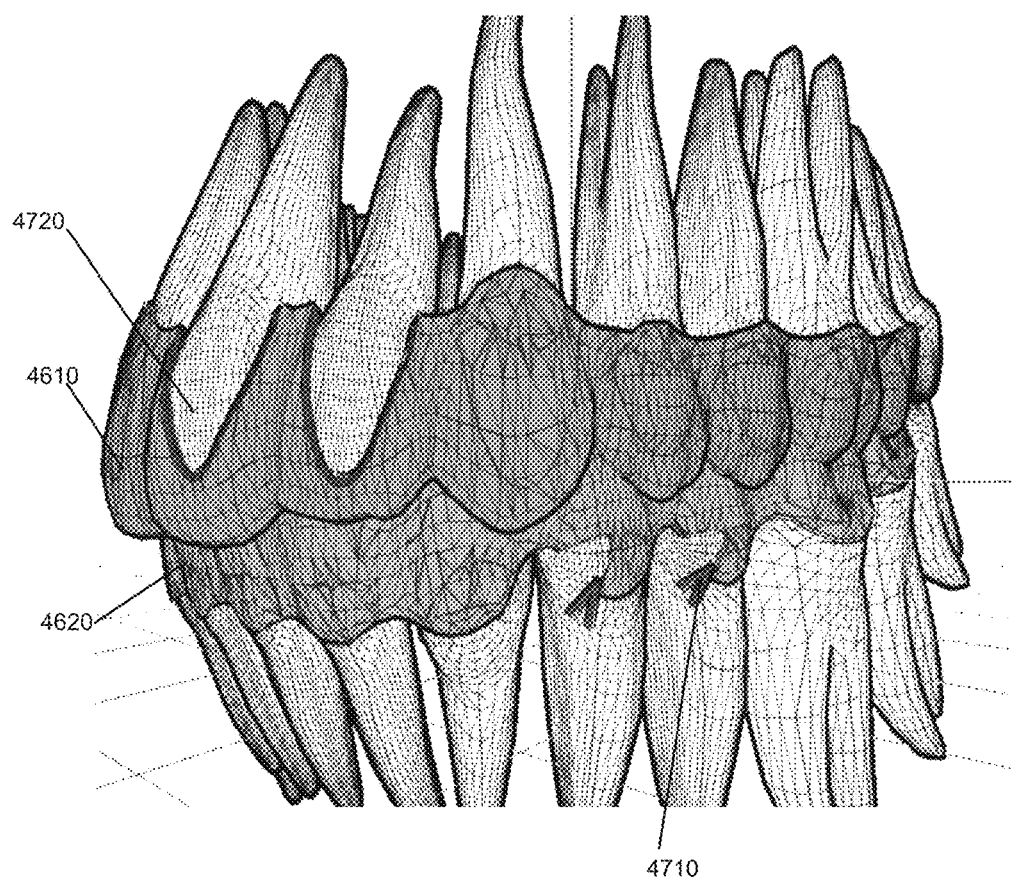

FIG. 46 shows an example 3D representation including an aligner 4610 on the upper row of teeth, and an aligner 4610 on the lower row of teeth. It should be noted that the contour lines on the 3D representation are illustrative only and may not be displayed as part of a 3D representation. As illustrated in FIG. 46, although the aligner may be defined by multiple aligner portions, in some examples, generating and/or displaying the 3D representation may generate and/or display an aligner which appears as a single unit. In some examples, the aligner portion parameters and modifiers may size and position each aligner portion model such that they abut without any visual gap.

In some examples, the aligner portion parameters and modifiers may size and position each aligner portion model such that they overlap but are not displayed having any noticeable overlap. In some examples, the processor(s) can be configured to not generate and/or display aligner portion borders or outlines for overlapping aligner portions.

In some embodiments, the aligner portions may be displayed as colors or shading. In some examples, the aligner portions may be displayed transparent or translucent such that one or more teeth underlying the aligner/aligner portion are visible.

Figure 47:
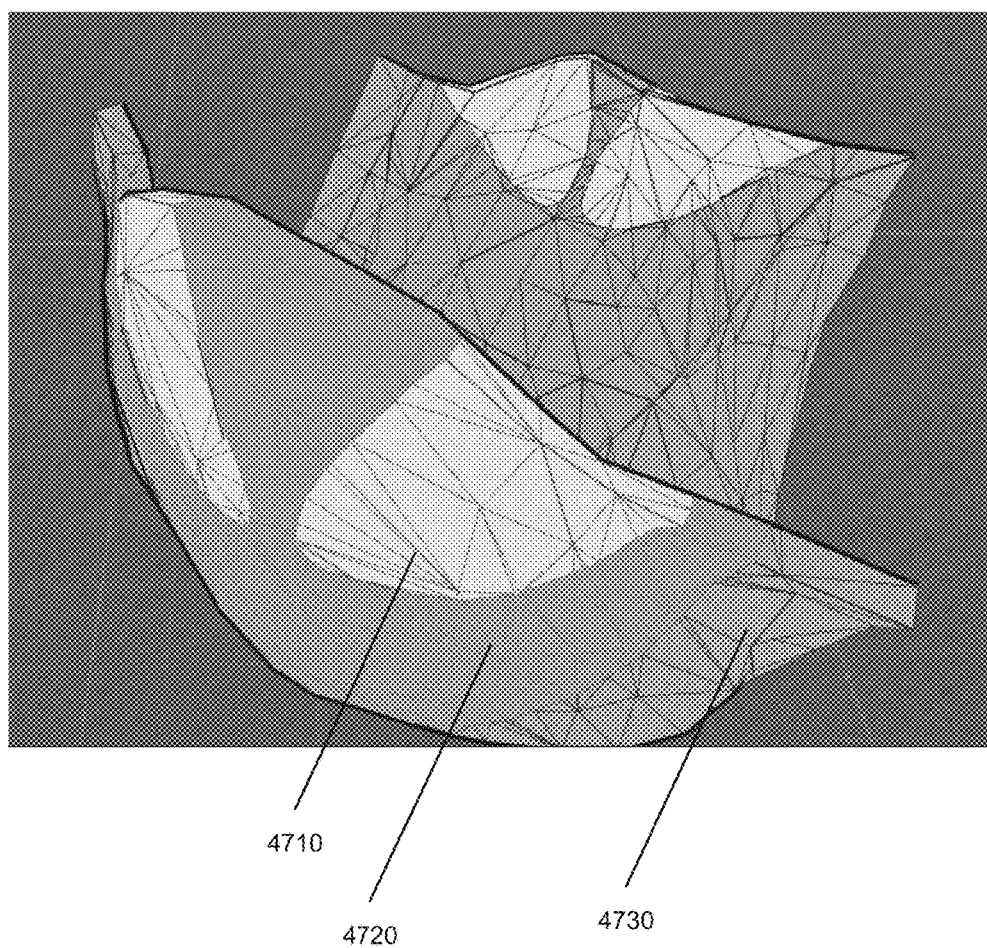

FIG. 47 shows an example 3D representation of an aligner portion corresponding to a particular tooth. In some embodiments, an aligner portion can include one or more sub-portions, cut-outs or otherwise smaller portions of an aligner. In some examples, removal of such a cut-out 4710 for receiving an elastic, or a cut-out 4720 for a tooth button or hook. FIG. 47 shows examples of such cut-outs 4710, 4720 which have not be removed but are colored for illustration, and FIG. 46 shows the cut-outs 4710, 4720 having been removed.

In some examples, an aligner portion can be associated with object identifier(s) identifying a base 3D model visually representing various smaller portions of the tooth's aligner portion. For example, the dental data set can include identifiers identifying a 3D model with at least one cut-out removed 4730, and a 3D model 4710, 4720 for each of the at least one cut-out. In some examples, an aligner portion may be defined by cut-outs on different sides of a tooth.

In some embodiments, each aligner cut-out may be treated as an individual aligner portion.

In some examples, having predefined cut-outs, sub-portions or otherwise smaller portion models, the processor(s) can define and generate such smaller portions more quickly and may require less data storage space to store a dentition representation (e.g. compared to custom defining the exact contours of a cut-out).

In some embodiments, an entire aligner (e.g. for an upper jaw or a lower jaw) may be defined by a template data set such that the parameter and modifiers for an entire aligner may be added to a dentition all at once.

In some embodiments, upon adding or adjusting at least a portion of the aligner (or adding or adjusting any other appliance such as a wire, bracket, button or other leverage/constraining device), the processor(s) can generate charting text indicating at least one tooth affected by the aligner, a value indicating a position of the affected tooth, a value defining a magnitude of impact on the position or orientation of the affect tooth, etc.

In some embodiments, upon receipt of a view-change input, the processor(s) can be configured to regenerate and/or redisplay the dentition with the aligner overlaying the teeth in the new view. In some examples, certain views such as unrolled or panoramic views or views where teeth are displayed with gaps in between (see, for example, FIG. 35) may be displayed with the aligner portions with visible gaps between them based on the position/orientation of the underlying teeth.

In some instances, the use of parameters for separate aligner portions can allow for relatively simple manipulations by the processor(s) to display the aligner portions overlaying teeth in any view and as view change inputs are received. In some examples, this may allow for real or near real time display of an updated 3D representation as view change inputs are received.

Alternatively, for views where teeth are spaced apart, in some embodiments, the processor(s) may generate and display a 3D representation by filling in the gaps between the aligner portions to provide a more natural visual indication of a continuous aligner.

In some embodiments, modifiers and/or parameters may define an attribute for an aligner attachment or other leverage device. In some examples, an aligner attachment can be a small leverage point glued onto teeth under an aligner to provide surface(s) on which the aligner can increase force(s) in certain directions on the teeth. In some examples, leverage devices can include buttons, hook brackets, elastics and/or other leverage devices for an underlying tooth and/or an aligner cut.

In some examples, a user can interact directly with a visual representation such as a 3D object. In some examples, direct model interaction can be used as an input to select a location for a marker or to select an area. Selected objects, or locations or areas of a selected object can, in some examples, be used to define a location of a restoration (dental filling) or crown, or a tooth condition such as a cavity, calculus or discoloration. Upon receiving an associated edit input, parameters can be created or modified to define the selected area and the type of restoration or crown.

In some examples, inputted markers can be used to create a smoothed outline which can be filled in with a color or texture.

Figure 18:
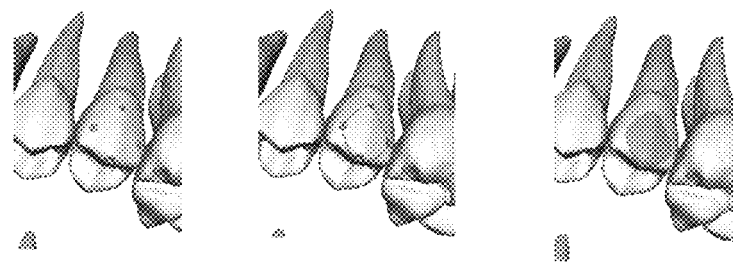

When a visual representation of the dental data set is displayed, the parameters can, in some examples, to render a surface or portion of a tooth including the restoration. FIG. 18 shows example visual representations wherein an area is selected and highlighted. In some examples, restorations or oral conditions can be displayed having different textures, or colors. In some examples, different colors can be used to represent a type of restoration, such as a composite resin, amalgam, porcelain, gold, or glass ionomer cement. In some examples, the colors and their corresponding material may be customized, such that a color for a particular material can be modified, and new colors and materials may be added.

These restorations may also be added to an object by use of templates which define, using standardized dental terminology, the location of the restoration, whereby the program stores the location of the markers used to show the area representing the restoration internally. These may include Class I, Class II, Class III, Class IV, Class V, or class VI restorations as commonly understood by dentists. When a user adds a restoration by this method to a specific tooth, they may only be required to input the material which the restoration is composed of.

Figure 19:
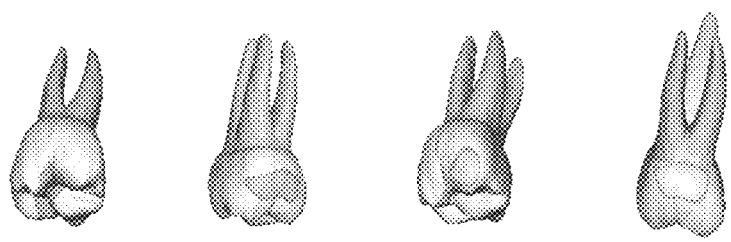

In some examples, color-coded regions of the tooth may also represent a dental condition, such as plaque, tooth decay, calculus, or periodontitis. A dental practitioner may, for example, create a region on a tooth of a particular color, and add a note to it, and in some examples can allow flexibility in interpretation. FIG. 19 shows example visual representations of teeth for identifying different conditions or restorations. These parameters can be applied to any number of teeth in either dental arch. Parameters can be applied to more than one tooth, when the operator, for example, provides corresponding inputs at each tooth separately to creating the mark on the tooth. In some examples, more than one region may be selected on any individual tooth. In some examples, when there is an overlap between selected regions, the system can uses digital compositing to combine the colors of the different regions.

In some examples, a similar procedure can be used to provide an input to adjust parameters for the gum model, to mark a region, for example, denoting the condition of gingivitis.

Figure 20:
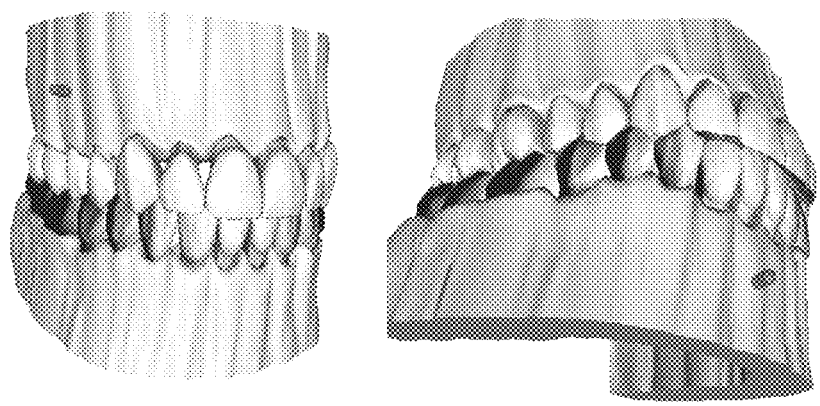
Figure 21:
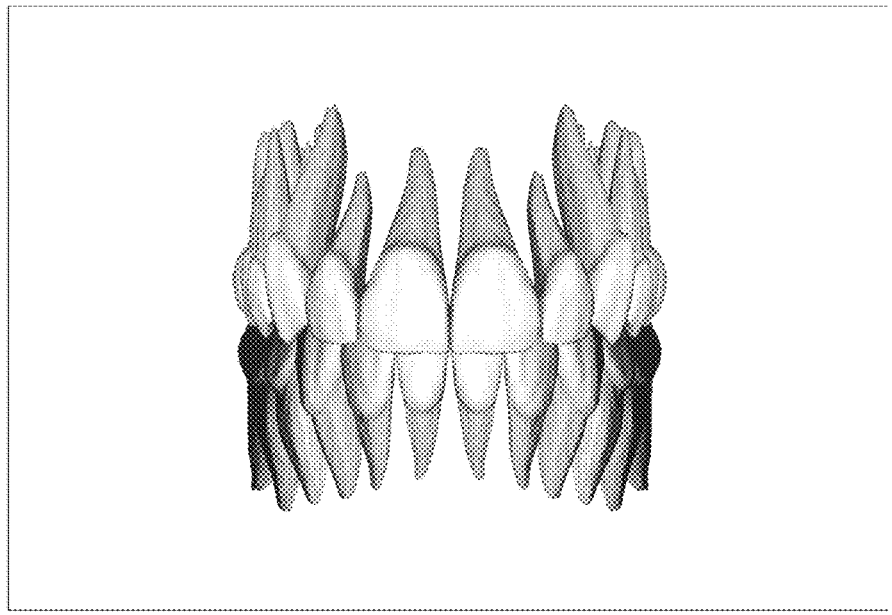

In some examples, inputs such as direct model interaction can also be used to select a location for a temporary anchorage device on the bone model. The operator can, for example, click on any location of the 3d model to mark where a temporary anchorage device should be shown on the data set. Any number of temporary anchorage devices can be applied to one or both dental arches. FIG. 20 shows example visual representations of a dental data set including temporary anchorage devices.

Similarly to the gum model, in some examples, a region of the bone model may be selected, for example to mark bone loss, or any other condition, as determined by the adjusted parameter and corresponding color associated with the parameter value.

In some examples, any number of the parametric and 3d model interaction modifications discussed herein can be applied in combinations, such that many possible dental or medical 3D visual data sets can be created. In some examples, applied parametric changes may be reversed, by selecting the opposing option, or removing the respective mechanism or mark from the dental or medical 3D visual data set or with an undo button. For example, a complicated dental data set may include several malocclusions, tooth removals, implants, brackets, wires, elastics, springs, and aligners (among the other modifications discussed), and each may be removed, modified or reversed, as the course of the patient's treatment progresses.

In some examples, parameters and/or modifiers can be indicate an interproximal reduction whereby a tooth surface is shaved off to provide more space for teeth to move and adjust their position relative to each other. The parameters and/or modifiers can define the size/location/shape of the interproximal reduction.

In some examples, a dental data set can be stored automatically with every parameter adjustment or at preset intervals, or manually when requested by a user. At block 340, a dental data set including all the adjusted parameters can be stored at a client or central device in an electronic database or otherwise. For greater clarify, storage of the dental data set can, in some examples, include storing automatically-generated or manually-entered charting text.

After creating and storing the dental data set the first time, subsequent times when the dental practitioner requires access to the dental data set, it can be retrieved from the electronic database. Additional modifications to the model can also be stored in the electronic database for later retrieval. In some examples, documenting the progress of a treatment or series of treatments can be managed by creating multiple dental data sets at different times. In some examples, a complete history of all parametric changes can be stored. In some examples, a user can retrieve previous dental data sets as required, to make comparisons or to aid in patient communications. The default retrieval of a dental data set can, in some examples, retrieve the most recent dental data set. In some examples, each dental data set or stages of the dental data set can be stored along with the date and time at which the data set was created or modified. In some examples, the dental data set can be link to or can include patient information.

In some examples, one or more processors may be configured to generate one or more snapshots of a patient's history by generating signals for displaying or printing one or more 3D visualizations of the data set at a specific time. These visualization(s) can be displayed or printed alongside at least a portion of the charting text associated with the data set at that time.

Figure 39:
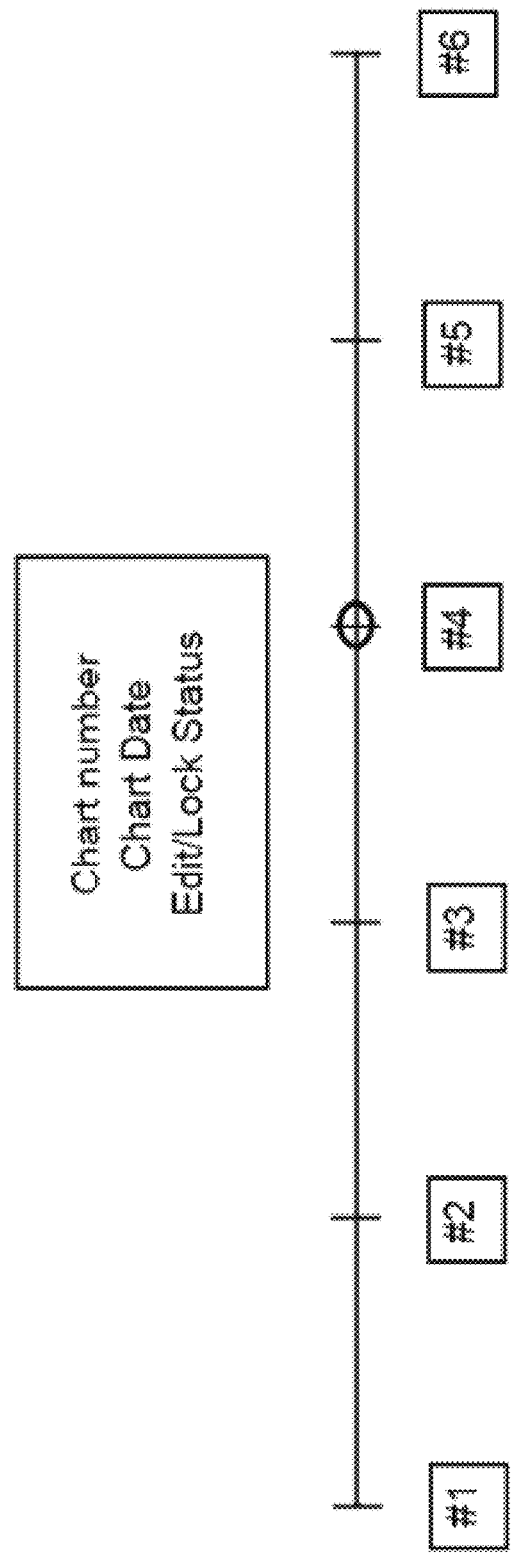
FIG. 39 shows an example user interface element.

In some examples, a user can traverse among several related dental or medical data sets, such as ones created for one patient at different times of the treatment, using a simplified user interface element where a representative piece of information for each data set is shown in a collection, and the data sets are ordered chronologically. The representative information may include the number of the data set (e.g. starting at number one for the first data set created), or the date. Navigating among the data sets may be performed using this user interface element, and when the navigation is performed, the other parts of the program, including the menu system and the 3d module, may be updated with the information contained in the chosen dental or medical 3D visual data set. The user interface element shows the current working data set, as well as some information associated with the current working data set, such as the creation time and date, the number of the data set, and the edit/lock status of the data set. The program may, in some implementations, prevent further modification of data sets that exceed a certain age, where age is defined as the time which a particular data set has existed since it was first created. In the case that a data set's age exceeds a predefined limit, such as 24 hours, the data set may have an edit/lock status of 'locked' and further modifications will not be allowed. If the data set's age is under the predefined limit, the edit/lock status of the data set may be 'editable', and the user will be allowed to make further modifications to the data set as required. FIG. 39 illustrates an example structure of such an interface element.

Figure 40:
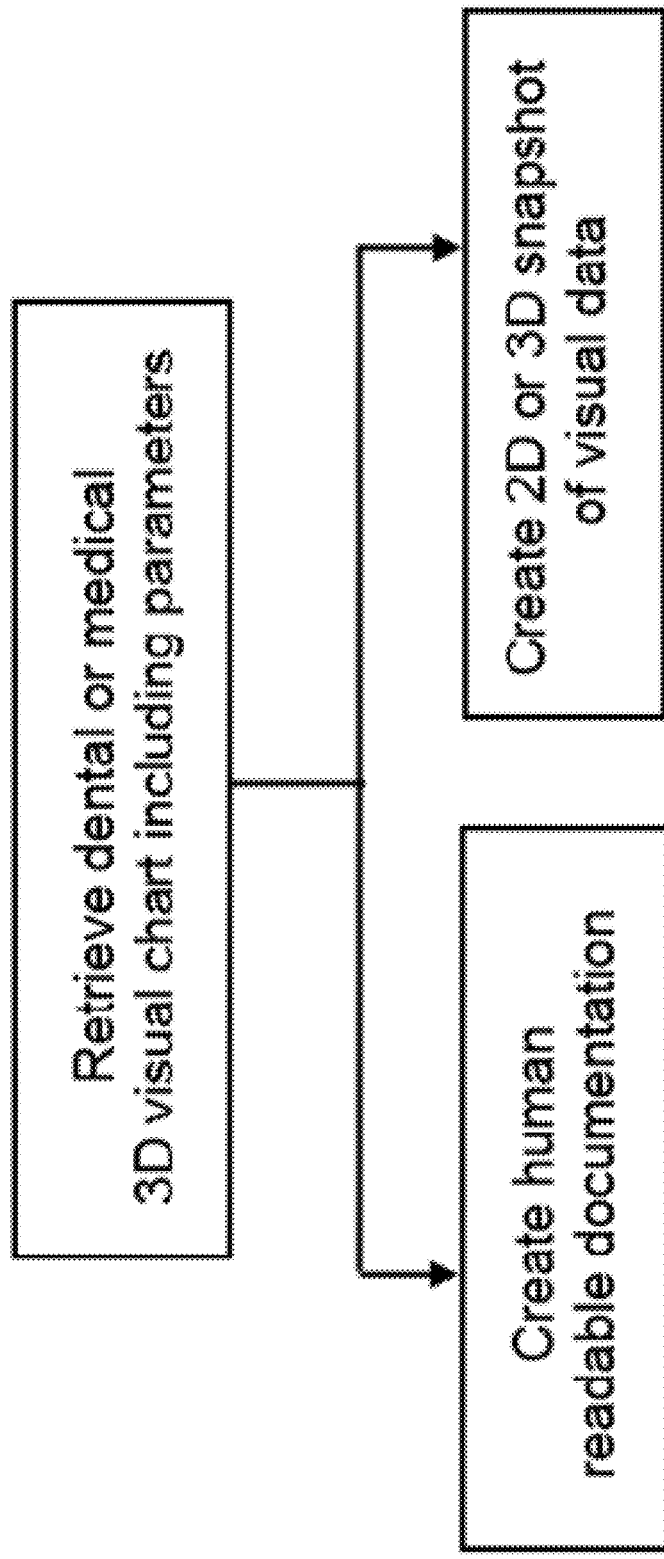
FIG. 40 shows a flowchart illustrating aspects of an example method for converting dental information.

In some examples, a single or multiple dental or medical data sets may be converted into an independent, standalone format by the program as shown in FIG. 40. This conversion may take all, some, or a condensed form of the information contained in the data set(s), parametric and otherwise, and transform it to an alternative textual or visual representation. In some implementations, this conversion may take each data set individually and extract information which shows the differences of that data set in comparison to the base model, such as all objects added or removed, all markings created, and all notes attached to the data set or to data set objects. In other implementations, the program may take a series of data sets, and convert them to information which represents the change or modification of each data set in comparison to the data set created previously in the chronological sense. For the first data set, for which there is no chronologically previous data set, the modifications are reported relative to the base model. The output of this conversion may be human-readable text, which may be a documentation of the patient treatment, and may contain associated information, such as the dates and times of all data sets, their contents, and their edit/lock status. This text may be in a plain-text format (ASCII), or it may be in a formatted-text format. The conversion may create a file of a proprietary or an open format directly (such as a Microsoft Word file), or it may open an instance of a proprietary software, such as one used for word-editing, and fill the document with the output of the conversion. FIG. 41 shows an example of an output that is a formatted document created automatically using the Microsoft Word automation interface. The output file may, depending on the format and capability of the proprietary format, be marked as a 'final revision' or with 'restrict editing', preventing the user from making any modifications to the file.

In some examples, the conversion of the data set into an alternate format may be initiated by the user, and in others, it may be automatic, creating and storing a human-readable record of the user actions. As described herein, this may occur as each user action occurs, after a dental or medical 3D visual data set is created and altered, or at the time the program is closed. This record may be stored on the local machine 110 or on a remote machine 120 as in FIG. 1. The information may be communicated to a subsystem of the program, or it may be communicated to another software working together with the program.

Figure 42:
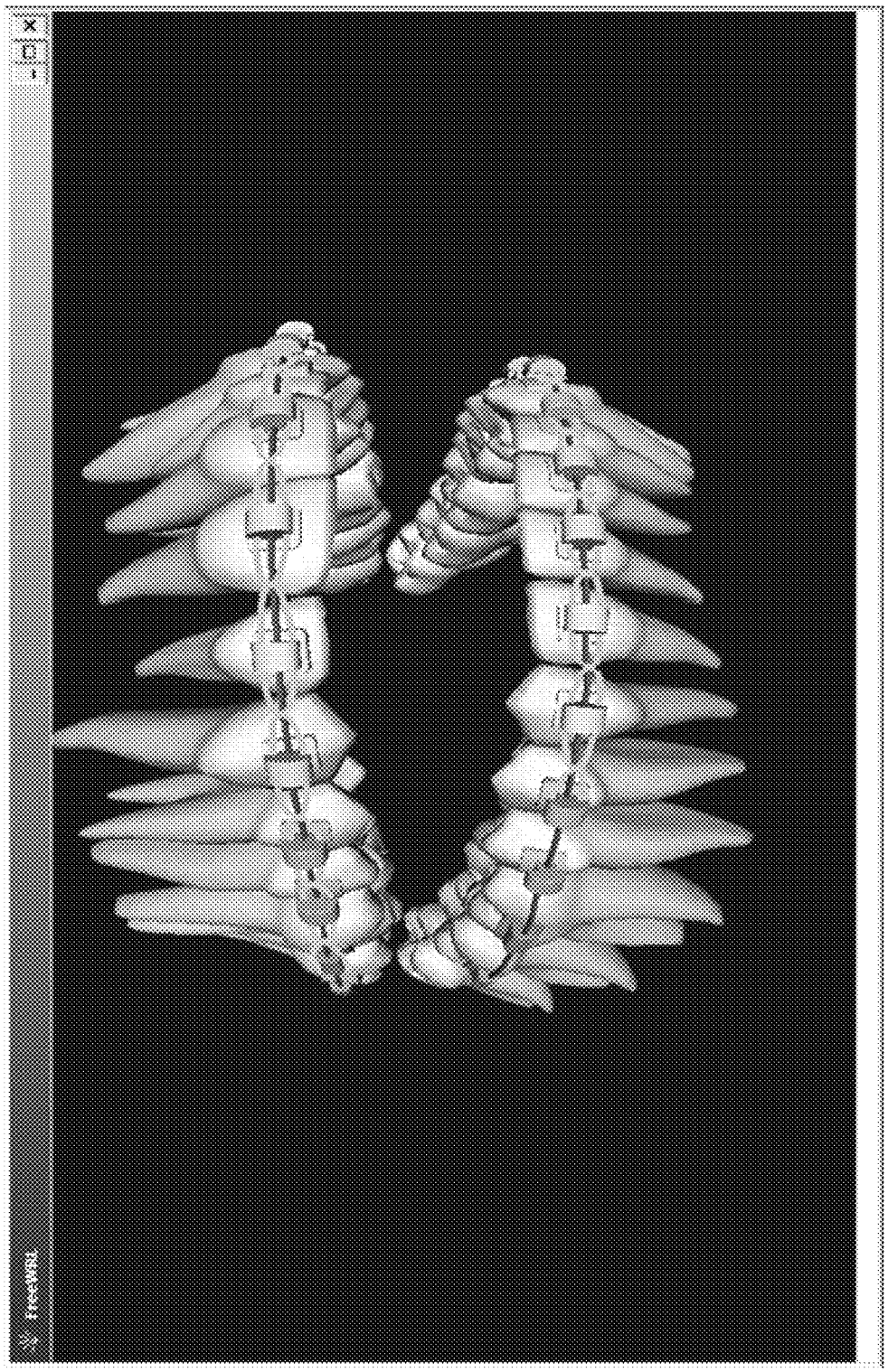

In other examples, the conversion may create an output that is of a visual format, such as a format used for representing 2D or 3D computer graphics. FIG. 42 shows an example of a data set exported to the X3D file format, and viewed in an independent viewer FreeWRL. The data may be exported in a 2D format as an image, such as a png or jpeg. In these examples, the output is a 'snapshot' of the data set, and can no longer be modified by adjusting parameters or otherwise. These files can be distributed and stored independently of the program and the original data set used to create them.

In some examples, the system can store the dental data set in a text format such as Extensible Markup Language (XML). In some examples, dental data sets can be stored in an electronic database and can be accessed for example via structured query language (SQL).

In some examples, the dental data set can be primarily parametric information such as parameters and values. By not including model or image information, some example dental data sets can be compact in size, and can, in some examples, be more efficient to store, backup, access or transfer.

At block 316, in some examples, a visual representation of a portion of a dental data set can be displayed in 3-dimensional form as illustrated for example in FIGS. 7A-D, 8-12, 13A-D, 14A-B, 15A-D, and 16-21. In some examples, the system can use a software or hardware 3D accelerator to display the 3D representation. In some examples, a 3D model can allows the user to see the mouth model in perspective view wherein objects closer to the camera appear bigger. Photorealistic or non-photorealistic rendering techniques can be used individually or combined. Photorealistic techniques can, in some examples, include color-shading the models to simulate light-reflection, or using life-like textures and bump maps. Non-photorealistic techniques can, in some examples include rendering orthodontic brackets and wires, aligners, or using color-coding. In some examples, these techniques can make it easier for the office staff to differentiate between different mechanisms used.

In some examples, 3D representations can provide information regarding the positioning of a dental arch, or regarding areas of contact between teeth. In some examples, this visual representation of dental arch positioning or areas of contact between teeth may not be available using traditional dental charting techniques.

Figure 22:
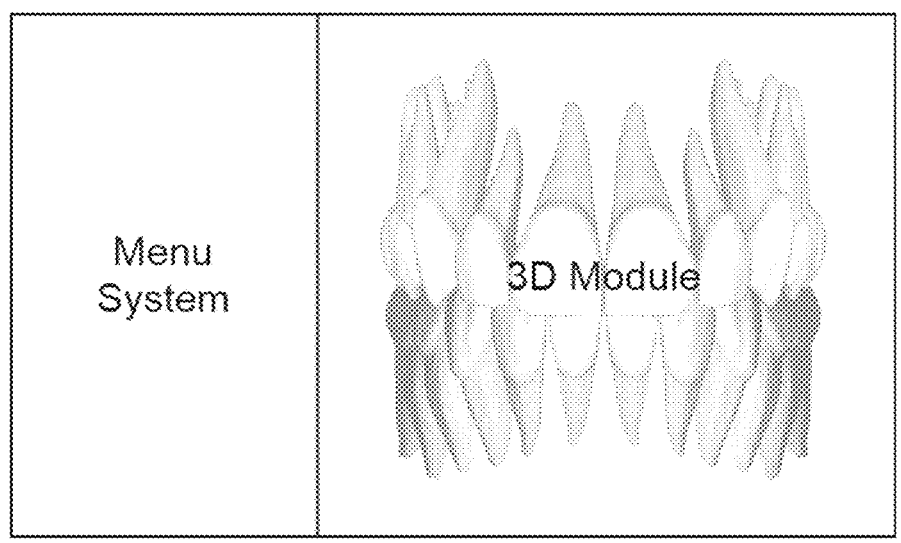
FIG. 22 shows an example view of a display for interacting with an example system.

In addition to the 3D module (described above), in some examples, the display can contains an area of the screen used for a menu system (see, for example FIG. 22).

In some examples, the menu system can be displayed in a dedicated area of the program screen, or, in some examples, it may be brought on-screen by an input (a pop-up menu). In some examples, both the menu system and the visual representation can be used to provide inputs for adjusting parameters in a dental data set.

Figure 23:
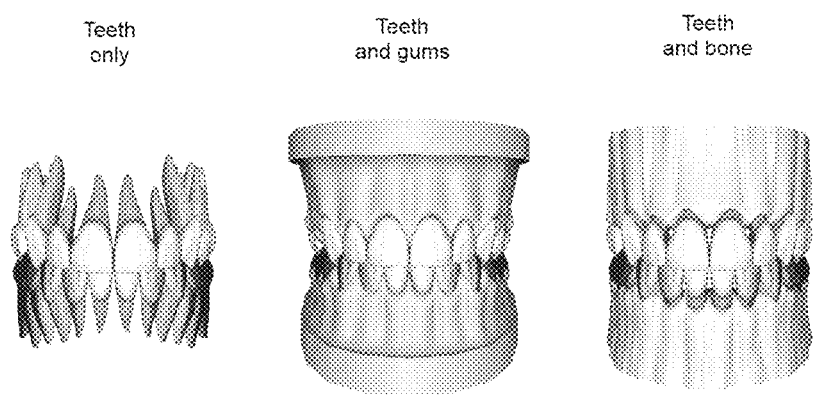

In some examples, the dental data set can include the dental arches of the maxilla or mandible. In some examples, the dental data set can include models for the surrounding bone and gums (see, for example, FIG. 23).

Figure 44:
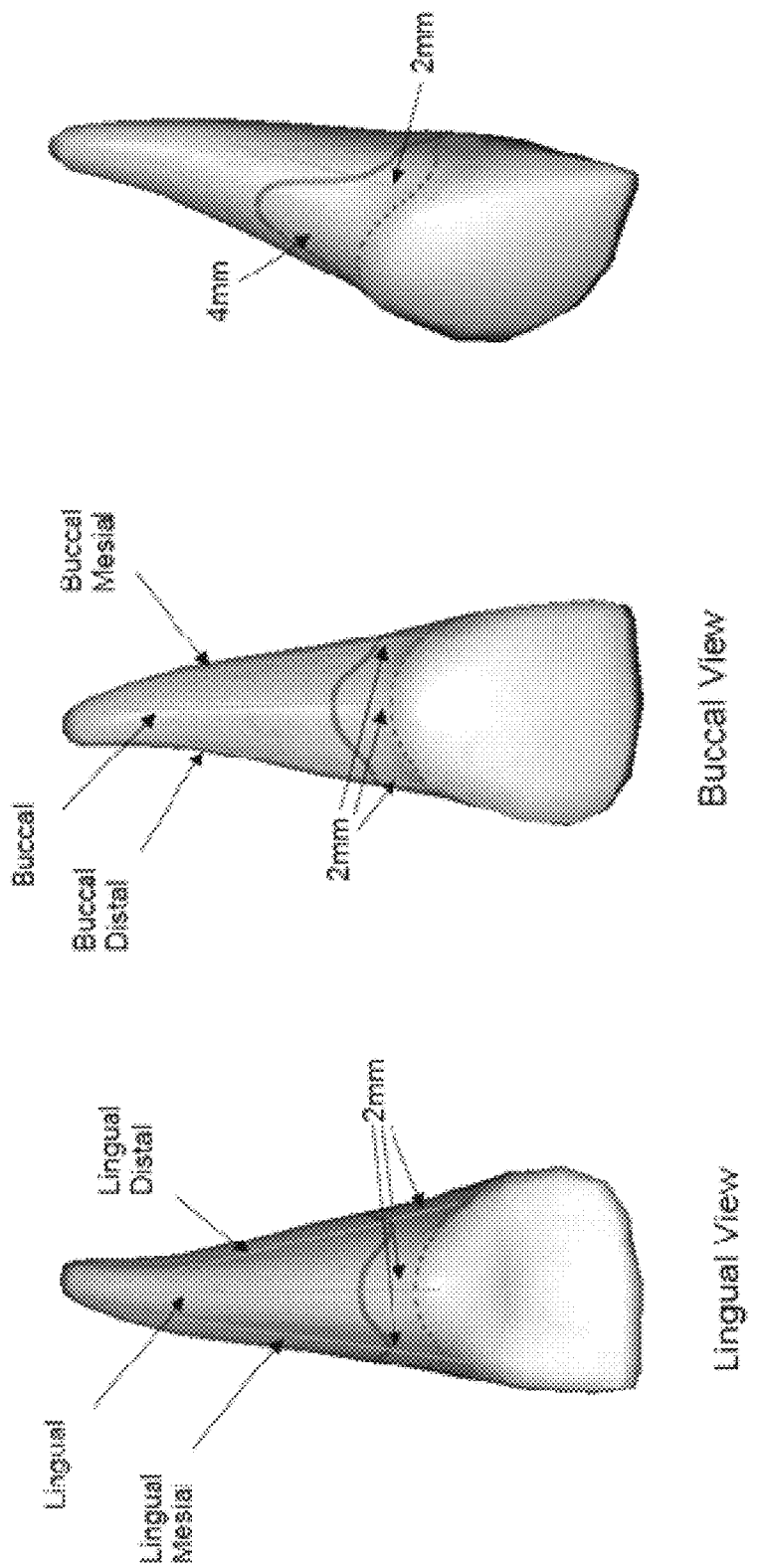

In some examples, parameters can include periodontal measurements which can be used to show a corresponding boundary of the periodontal ligament on each tooth. In some examples, periodontal measurements can be inputted as 6 length measurements representing periodontal pocket depth at certain locations on the surrounding sides of the tooth. In some examples, a boundary of the periodontal ligament can be displayed as a color-coded line, mark, or area on the model of each tooth. The periodontal measurements can be relative to a base curve that runs around each tooth and represents where bone tissue begins on an average tooth, as seen in FIG. 43. The measurements may occur along 6 imaginary lines, for which markings are stored internally in the software, starting at the base curve. A given periodontal measurement can be measured along its corresponding line, along the surface of the tooth. An example of these lines is shown in FIG. 44. In some examples, these lines may not be straight and may conform to the surface of the tooth. The boundary of the periodontal ligament can be determined using the six measurements, which are then connected by the program to yield a smooth curve. The parameters may be defined in terms of their granularity (in 1 mm increments), and a maximum value (such as 6 mm). In one implementation, a user may interact with the periodontal line directly by dragging one of the six markers up or down the marking line (which may be shown explicitly with tick marks representing 1 mm distances).

In some examples, the system can operate in substantially real-time, such that it takes minimal time for parameters to be adjusted and an update 3D visual representation to be displayed when an edit input is received.

In some examples, when displaying a visual representation, a device can create a 3-dimensional representation matching the parametric options. This can, in some examples, include all 3D object data required to render the dental data set onto an output device. These objects can include matrices of polygon vertex locations, normals, texture coordinates, and the like.

The 3D object data can, in some examples be rendered using a 3D accelerator to creates a 2-dimensional image, capable of being transmitted to an output device (a display, such as a television or computer screen). The result can be shown on the output device and in some examples, can provide visual feedback of changes made to the dental data set.

In some examples, system can include internal rules by which it can perform the rendering of a visual representation or simulation. These rules can, in some examples, make the interaction of the 3D objects in the visual representation approximate a patient's mouth, simplify the amount of user input required to make simulation changes, or limit the discretion of the user. Examples of these rules are described herein.

In one example, when a dental arch (maxillary or mandible) is adjusted, it can be refitted by the program. The adjustments can include, for example: an addition or modification of a malocclusion (such as a movement or rotation of a tooth with respect to its default position in the arch), a modification in the size of a tooth, the addition or removal of a gap between teeth, addition or removal of a tooth model, replacement of a tooth model with an implant or bridge, or the addition of a wire bend. In some examples, the refitting process can include rules to ensure that the dental arch appears correctly (without inadvertent overlaps in the 3d models). The refitting process can, in some examples, position the teeth models in pairs, starting at the incisors and working towards the molars, along a smooth curve which represents the dental arch. In some examples, for each pair, one tooth can be moved along the arch, starting at the distal end and progressing towards the mesial end, and the other remains stationary, until a position is found where the proper contact between the teeth is established, using a collision detection algorithm. In some examples, in the case of a gap, the contact position can be initially established, and the tooth can be moved back towards the distal end of the arch to create a gap of the appropriate distance.

In some examples, malocclusion options, such as the apical-coronal movement, the buccal-lingual movement, the mesial-distal rotation, the apical-coronal rotation, and the buccal-lingual rotation, can be performed using a series of markers attached to each tooth model. For example, the apical-coronal movement can approximate a movement along the root-crown axis of the tooth, to reflect different teeth (such as the incisors versus the molars) having a different 'tilt' with respect to the dental arch. In another example, the buccal-lingual movement can be performed by moving the tooth in a direction that is normal (90 degrees) to the arch on which it is placed. The mesial-distal rotation can be performed about an axis that is normal to the arch. The apical-coronal rotation can be performed about an axis passing through the root-crown axis of the tooth, and the buccal-lingual rotation can be performed about an axis that is parallel to the tangent of the arch, passing through a marker representing the wire.

In some examples, after the dental arch is positioned, the orthodontic brackets (if added by the user) can be positioned at a pre-determined location on the surface of each tooth. Similarly, an aligner, after the dental arch is positioned, can be positioned at a predetermined location relative to the teeth. In some examples, this can ensure that each bracket is shown by default on an appropriate location on the outside of the arch, allowing wire segments connecting the brackets to be more easily rendered. In some examples, the default bracket positions can be modified by moving them in 0.5 mm increments (from −4 mm to +4 mm) along the mesial-distal axis of the tooth, along the apical-coronal axis of the tooth, or rotating them about the buccal-lingual axis of each tooth (in 2.5 degree increments, from −15 to +15). In some examples, these movements can be performed using 3d markers attached to each tooth, such that each movement is a rotation around the tooth, approximating the round surface of each tooth using a circle. The rotation can, in some examples, be performed about the wire marker of the bracket. Lingual buttons and bite turbos can be positioned similarly to the brackets by using a predetermined location on the surface of each tooth.

In some examples, a plurality of aligners can be used, and the position of the aligner can be modified to reflect a change in aligned in the court of a treatment plan. IN some examples, the aligner can be replaces with a differently-sized aligners. In some examples, the aligners can be numbered to distinguish between differently-sized aligners in a treatment plan.

Figure 45:
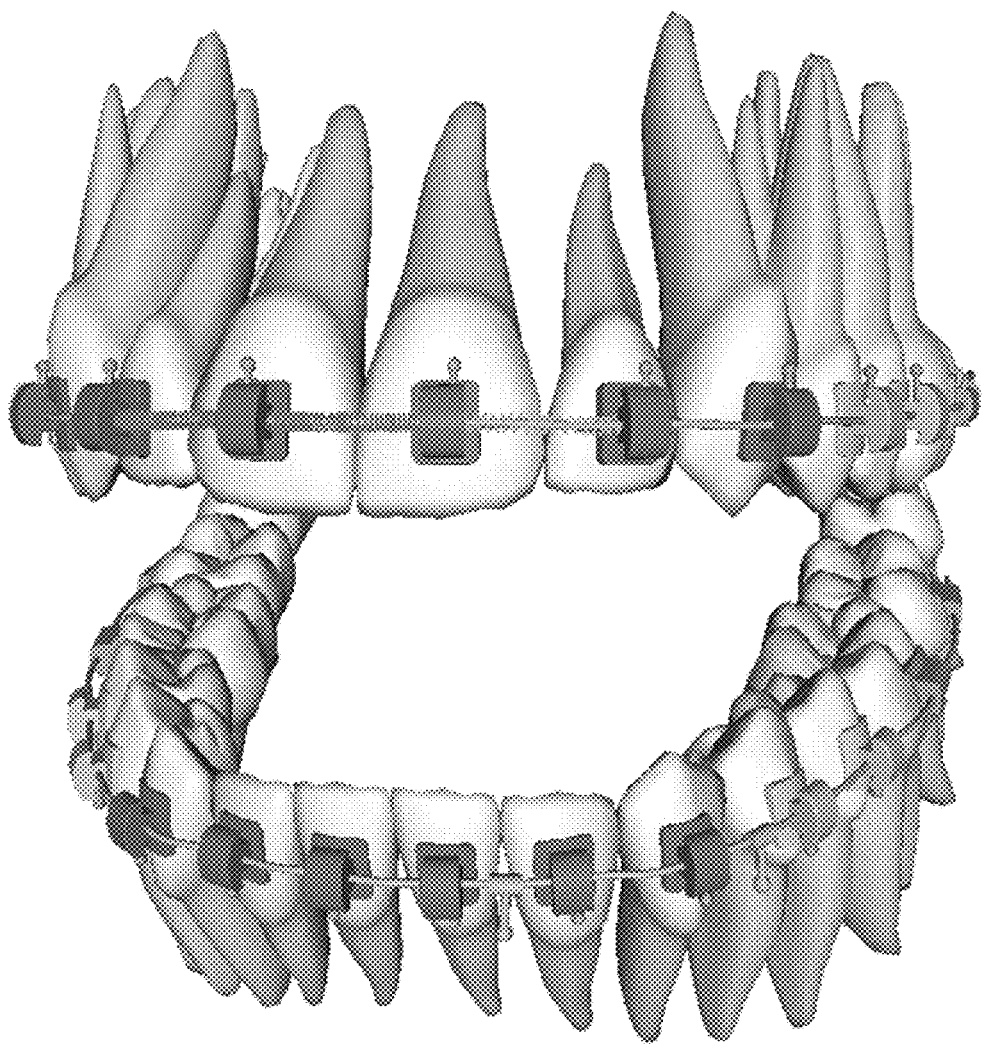

When rendering orthodontic wires, the system can, in some examples, use two 3d markers attached to each bracket (one on each side), such that, no matter how the teeth and brackets have been placed, the wire can always attach to the same location on the bracket. For each wire segment (a piece of wire rendered between each two consecutive orthodontic brackets), the system can use the bracket markers to create a smooth curve, and can approximate the bend that is created in the wire by the wire slot of each bracket. Wire springs can be rendered using the same curve, such that they appear to 'wrap' the wire segment to which they have been added. Wire hooks can be similarly positioned along this curve, and can use the tangent and normal to this curve to position themselves along the wire. See FIG. 45 for an example.

In some examples, each bracket, wire hook, bracket hook, temporary anchorage device and lingual button, can have internal 3d markers for elastic connections, which can be used to show an approximate 'wrapping' of an elastic that has been connected to it and other objects.

In some examples, the dental data set can be linked to an x-ray, image or other information regarding a patient's dentition.

In some examples, information that is input to the system may be non-parametric, such as of a textual or auditory format. The program may accept such information, and create an internal connection between such information and an object of the dental or medical 3D visual data set. The information may be of the form of a note or comment describing the condition or other relevant information of an object belonging to the data set. The system may store that information and display it to communicate that the information belongs to the data set object initially associated with the note or comment. The information may also belong to the data set as a whole, representing a 'general' comment on the data set or patient. This may include an allergy or other medical condition, the state of the patient's dentition, or other relevant aspect of the patient, such as oral hygiene or compliance with procedures given previously (such as wearing elastics consistently). The system may store any additional information with the inputted information, such as the date or the user who inputted the information. The form of the note or comments appended to the objects may also take the form of predefined statements, representing common procedures taken by a dental or medical practice, such that they may be selected as a parameter without the requirement to describe the procedure each time it needs to be appended to the data set. These predefined statements may be modified by the user to fit the needs of the practice in question.

In some examples, the parametric modeling described herein can be applied to other medical fields involving modeling and/or charting such as, for example, orthopedics, ophthalmology, cardiology, dermatology, or podiatry.

While the foregoing invention has been described in some detail for purposes of clarity and understanding, it will be appreciated by those skilled in the relevant arts, once they have been made familiar with this disclosure, that various changes in form and detail can be made without departing from the scope of the invention. The invention is therefore not to be limited to the exact components or details of methodology or construction set forth above. Except to the extent necessary or inherent in the processes themselves, no particular order to steps or stages of methods or processes described in this disclosure, including the Figures, is intended or implied. In many cases the order of process steps may be varied without changing the purpose, effect or import of the methods described.

The invention claimed is:

1. A method of charting dental information on an electronic device, the method comprising:
   generating or retrieving a dental data set representing at least a portion of a dentition, the dental data set including:

a set of base parameters including object identifiers and base values, each object identifier identifying a base three-dimensional (3D) models visually representing an individual tooth or implement, the base values defining default positions and orientations of each of the base 3D models in a dental arch, and a set of modifiers defining changes to visual aspects of one or more of the base 3D models relative to base parameters;

wherein the dental data set includes object identifiers identifying portions of an aligner;

generating a 3D representation of at least the portion of the dentition with each base 3D model in at least the portion of the dentition positioned relative to each other in the 3D representation based on the base values as modified by the modifiers;

displaying the 3D representation;

receiving an input based on an interaction with the 3D representation;

adjusting at least one of the modifiers based on the received input; and generating charting text based on at least one charting template associated with a dental activity corresponding to the received input.

2. The method of claim 1, wherein generating the 3D representation comprises generating the 3D representation with each portion of the aligner in at least the portion of the dentition positioned such that the 3D model of the aligner appears as a single unit.

3. The method of claim 1, wherein each portion of the aligner corresponds to a respective tooth that each portion of the aligner overlays.

4. The method of claim 1, wherein parameters associated with an aligner portion include at least one parameter or modifier for at least one cut-out, and wherein the 3D model corresponding to the aligner portion includes a 3D model for the aligner portion with the at least one cut-out removed and a 3D model for each of the at least one cut-out.

5. The method of claim 1 wherein the aligner in the 3D representation is displayed transparent or translucent such that one or more teeth underlying the aligner are visible.

6. The method of claim 1 wherein when the received input indicates a change to a modifier for a particular tooth, adjusting the at least one of the modifiers includes adjusting at least one modifier associated with a portion of the aligner corresponding to the particular tooth.

7. The method of claim 1 wherein modifiers associated with a portion of the aligner define an attribute for an aligner attachment or an aligner cut.

8. The method of claim 1 comprising upon adding or adjusting at least a portion of the aligner or other leverage device, generating charting text indicating at least one of: at least one tooth affected by the addition or adjustment, at least one value indicating a position of the at least one affected tooth, or at least one value indicating a magnitude of impact on the position or orientation of the at least one affected tooth.

9. The method of claim 1 wherein at least one modifier or parameter associated with a tooth defines at least one of: a shape, size or location of an interproximal reduction.

10. The method of claim 1 wherein when the 3D representation is for a view where teeth in at least the portion of the dentition are spaced-apart, the 3D representation is generated with both the teeth and corresponding overlaying aligner portions spaced-apart.

11. An electronic device for charting dental information, the device comprising:

at least one memory; and at least one processor configured for:

generating or retrieving a dental data set representing at least a portion of a dentition, the dental data set including:

a set of base parameters including object identifiers and base values, each object identifier identifying a base three-dimensional (3D) models visually representing an individual tooth or implement, the base values defining default positions and orientations of each of the base 3D models in a dental arch, and a set of modifiers defining changes to visual aspects of one or more of the base 3D models relative to base parameters;

wherein the dental data set includes object identifiers identifying portions of an aligner;

generating a 3D representation of at least the portion of the dentition with each base 3D model in at least the portion of the dentition positioned relative to each other in the 3D representation based on the base values as modified by the modifiers;

displaying the 3D representation;

receiving an input based on an interaction with the 3D representation;

adjusting at least one of the modifiers based on the received input; and generating charting text based on at least one charting template associated with a dental activity corresponding to the received input.

12. The device of claim 11, wherein generating the 3D representation comprises generating the 3D representation with each portion of the aligner in at least the portion of the dentition positioned such that the 3D model of the aligner appears as a single unit.

13. The device of claim 11, wherein each portion of the aligner corresponds to a respective tooth that each portion of the aligner overlays.

14. The device of claim 11, wherein parameters associated with an aligner portion include at least one parameter or modifier for at least one cut-out, and wherein the 3D model corresponding to the aligner portion includes a 3D model for the aligner portion with the at least one cut-out removed and a 3D model for each of the at least one cut-out.

15. The device of claim 11 wherein the aligner in the 3D representation is displayed transparent or translucent such that one or more teeth underlying the aligner are visible.

16. The device of claim 11 wherein when the received input indicates a change to a modifier for a particular tooth, adjusting the at least one of the modifiers includes adjusting at least one modifier associated with a portion of the aligner corresponding to the particular tooth.

17. The device of claim 11 wherein modifiers associated with a portion of the aligner define an attribute for an aligner attachment or an aligner cut.

18. The device of claim 11 wherein the at least one processor is configured for: upon adding or adjusting at least a portion of the aligner or other leverage device, generating charting text indicating at least one of: at least one tooth affected by the addition or adjustment, at least one value indicating a position of the at least one affected tooth, or at least one value indicating a magnitude of impact on the position or orientation of the at least one affected tooth.

19. The device of claim 11 wherein at least one modifier or parameter associated with a tooth defines at least one of: a shape, size or location of an interproximal reduction.

20. A non-transitory, computer-readable medium or media having stored thereon instructions which, when executed, cause at least one processor for:
  generating or retrieving a dental data set representing at least a portion of a dentition, the dental data set including:
    a set of base parameters including object identifiers and base values, each object identifier identifying a base three-dimensional (3D) models visually representing an individual tooth or implement, the base values defining default positions and orientations of each of the base 3D models in a dental arch, and
    a set of modifiers defining changes to visual aspects of one or more of the base 3D models relative to base parameters;
    wherein the dental data set includes object identifiers identifying portions of an aligner;
  generating a 3D representation of at least the portion of the dentition with each base 3D model in at least the portion of the dentition positioned relative to each other in the 3D representation based on the base values as modified by the modifiers;
  displaying the 3D representation;
  receiving an input based on an interaction with the 3D representation;
  adjusting at least one of the modifiers based on the received input; and
  generating charting text based on at least one charting template associated with a dental activity corresponding to the received input.

* * * * *